(12) United States Patent
Barodka et al.

(10) Patent No.: US 10,743,775 B2
(45) Date of Patent: Aug. 18, 2020

(54) DEVICE AND METHOD TO MEASURE VENTRICULAR ARTERIAL COUPLING AND VASCULAR PERFORMANCE

(71) Applicant: THE JOHNS HOPKINS UNIVERSITY, Baltimore, MD (US)

(72) Inventors: Viachaslau Barodka, Baltimore, MD (US); Yurie Obata, Sakai (JP)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 471 days.

(21) Appl. No.: 15/792,006

(22) Filed: Oct. 24, 2017

(65) Prior Publication Data

US 2018/0042494 A1    Feb. 15, 2018

Related U.S. Application Data

(63) Continuation-in-part of application No. 15/449,410, filed on Mar. 3, 2017.
(Continued)

(51) Int. Cl.
*A61B 5/02* (2006.01)
*A61B 8/00* (2006.01)
(Continued)

(52) U.S. Cl.
CPC ...... *A61B 5/02028* (2013.01); *A61B 5/02007* (2013.01); *A61B 5/0261* (2013.01);
(Continued)

(58) Field of Classification Search
CPC .. A61B 5/02; A61B 5/00; A61B 5/024; A61B 5/026; A61B 5/0295; A61B 5/044;
(Continued)

(56) References Cited

U.S. PATENT DOCUMENTS

| 8,428,720 B2* | 4/2013 | Corbucci | A61B 5/02028 607/19 |
| 2003/0109772 A1* | 6/2003 | Mills | A61B 5/02028 600/310 |

(Continued)

OTHER PUBLICATIONS

Desaive et al., Assessment of ventricular contractility and ventricular-arterial coupling with a model-based sensor. (2013) Computer Methods and Programs in Biomedicine, 109(2), pp. 182-189.

*Primary Examiner* — Eric J Messersmith
(74) *Attorney, Agent, or Firm* — MH2 Technology Law Group, LLP

(57) ABSTRACT

A device for measuring a ventricular-arterial coupling of a subject includes first and second inputs. The first input receives signals from a plurality of electrocardiogram sensors that are coupled to the subject at a plurality of first locations. The second input receives signals from a plurality of photoplethysmogram sensors that are coupled to the subject at a plurality of second locations. The second locations are selected from the group consisting of a head of the subject, an arm of the subject, and a leg of the subject. The signals received from the electrocardiogram sensors and the signals received from the photoplethysmogram sensors are received simultaneously. The device also includes a monitor configured to display the signals from the electrocardiogram sensors and the signals from the photoplethysmogram sensors.

20 Claims, 25 Drawing Sheets

Related U.S. Application Data

(60) Provisional application No. 62/302,884, filed on Mar. 3, 2016.

(51) Int. Cl.

| | | |
|---|---|---|
| *A61B 5/024* | (2006.01) | |
| *A61B 5/044* | (2006.01) | |
| *A61B 8/06* | (2006.01) | |
| *A61B 7/04* | (2006.01) | |
| *A61B 5/00* | (2006.01) | |
| *A61B 8/08* | (2006.01) | |
| *A61B 5/026* | (2006.01) | |
| *A61B 5/021* | (2006.01) | |
| *A61B 7/00* | (2006.01) | |
| *A61B 5/0452* | (2006.01) | |
| *A61B 5/0295* | (2006.01) | |
| *A61B 5/0205* | (2006.01) | |
| *A61B 5/0456* | (2006.01) | |
| *A61B 5/08* | (2006.01) | |
| *A61B 5/029* | (2006.01) | |

(52) U.S. Cl.
CPC ...... *A61B 5/02125* (2013.01); *A61B 5/02416* (2013.01); *A61B 5/044* (2013.01); *A61B 5/0452* (2013.01); *A61B 5/6815* (2013.01); *A61B 5/6823* (2013.01); *A61B 5/742* (2013.01); *A61B 7/00* (2013.01); *A61B 7/04* (2013.01); *A61B 8/065* (2013.01); *A61B 8/463* (2013.01); *A61B 8/488* (2013.01); *A61B 5/021* (2013.01); *A61B 5/0205* (2013.01); *A61B 5/026* (2013.01); *A61B 5/029* (2013.01); *A61B 5/0295* (2013.01); *A61B 5/0456* (2013.01); *A61B 5/082* (2013.01); *A61B 5/6824* (2013.01); *A61B 5/6826* (2013.01); *A61B 5/6828* (2013.01); *A61B 5/6829* (2013.01); *A61B 2562/04* (2013.01)

(58) Field of Classification Search
CPC .... A61B 7/04; A61B 8/00; A61B 8/06; A61B 8/08; A61B 5/0261; A61B 7/00; A61B 5/02125; A61B 5/0452; A61B 5/02028; A61B 8/463; A61B 5/02416; A61B 8/065; A61B 5/02007; A61B 5/6815; A61B 5/6823; A61B 8/488; A61B 5/742; A61B 5/6829; A61B 5/0205; A61B 5/021; A61B 5/029; A61B 5/0456; A61B 5/082; A61B 2562/04; A61B 5/6824; A61B 5/6826; A61B 5/6828
See application file for complete search history.

(56) References Cited

U.S. PATENT DOCUMENTS

| | | | |
|---|---|---|---|
| 2003/0163058 A1* | 8/2003 | Osypka | A61B 5/02007 600/513 |
| 2004/0077934 A1 | 4/2004 | Massad | |
| 2011/0009712 A1* | 1/2011 | Fayram | A61B 5/0084 600/301 |
| 2017/0238818 A1* | 8/2017 | Gaurav | A61B 5/02125 |
| 2018/0235567 A1* | 8/2018 | Bezemer | A61B 5/02125 |

\* cited by examiner

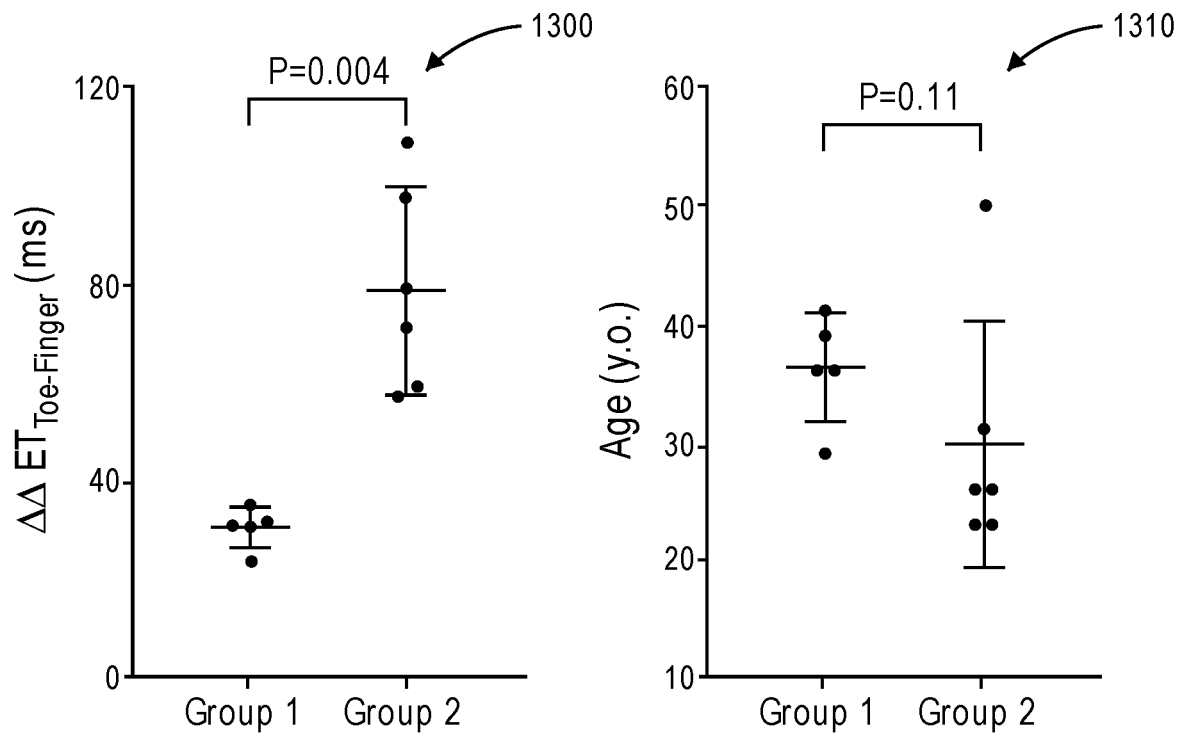
FIG. 13A
FIG. 13B
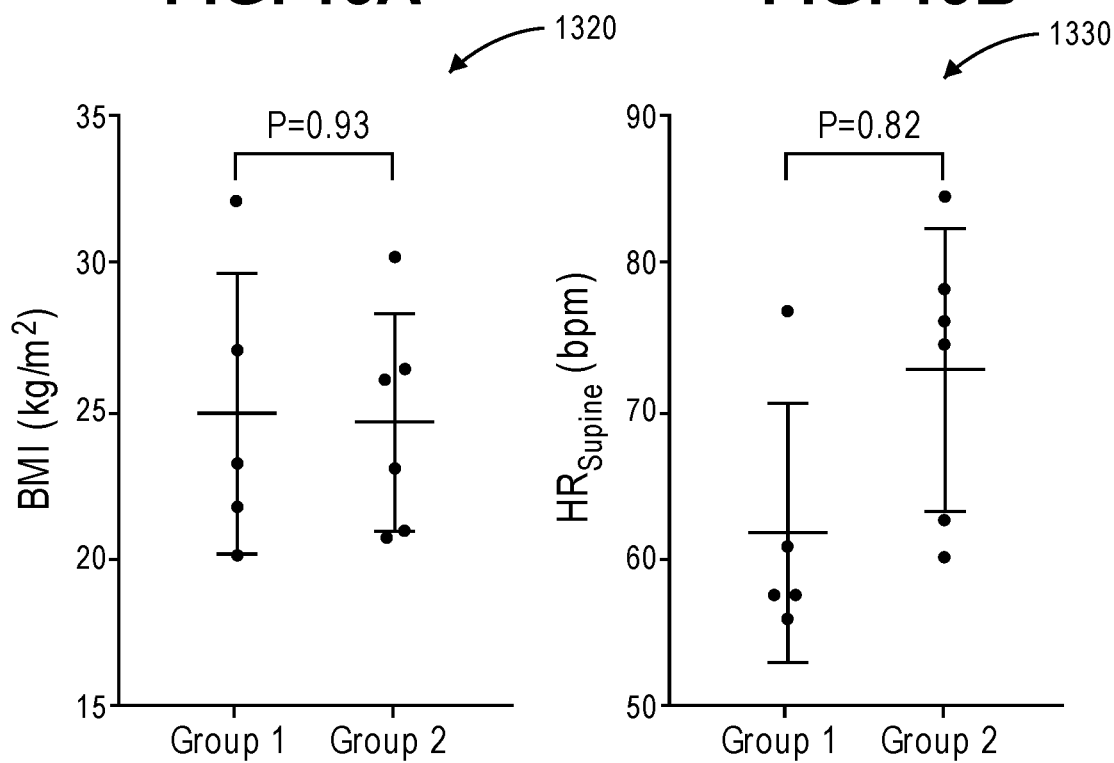
FIG. 13C
FIG. 13D

FIG. 13E     FIG. 13F

DEVICE AND METHOD TO MEASURE VENTRICULAR ARTERIAL COUPLING AND VASCULAR PERFORMANCE

CROSS-REFERENCE TO RELATED APPLICATIONS

The present application is a continuation-in-part of U.S. patent application Ser. No. 15/449,410, filed on Mar. 3, 2017, which claims priority to U.S. Provisional Patent Application No. 62/302,884, filed on Mar. 3, 2016, each of which is hereby incorporated by reference in its entirety.

FIELD OF THE INVENTION

The present invention relates generally to hospital management. More particularly, the present invention relates to emergency and operating room management to support an objective triage evaluation.

BACKGROUND OF THE INVENTION

In clinical practice, hemodynamic monitoring during anesthesia and in intensive care units is often employed. The goal of hemodynamic monitoring is to guide interventions as well as to ensure adequate end organ perfusion and oxygen delivery by optimizing stroke volume (SV) and cardiac output (CO). Conventional hemodynamic variables such as arterial blood pressure, central venous pressure, and urine output are frequently used as surrogates for adequate end organ perfusion. However, these parameters are not able to directly measure SV and, hence, CO. Although the pulmonary artery catheter (PAC) is still considered the gold standard to monitor SV and CO, its invasive nature and potential for life-threatening complications largely restrict its use in the modern era. Recently, multiple non-invasive or minimally-invasive SV/CO monitoring devices have been introduced into clinical practice, such as pulse contour analysis devices, esophageal Doppler devices, the partial carbon dioxide rebreathing technique, and transthoracic electrical bioimpedance measurements. However, they have not yet replaced PACs due to poor trending ability and inadequate agreement with the clinical standard (e.g., PAC). Meanwhile, echocardiography, transesophageal (TEE) or transthoracic (TTE), has become a frequently utilized monitoring method, especially in cardiac operating rooms and intensive care units. TEE-based SV/CO has been validated against PAC-based values with good limits of agreement. While ultrasound-based techniques have a number of advantages, they have several important limitations, such as the difficulty of continuous real-time monitoring, interference from electric cautery, and operator dependence. Moreover, TEE is an invasive technique and is poorly tolerated by un-sedated patients. In addition, another drawback of TEE compared to pulmonary artery catheters is the inability to measure real-time SV and CO. There have been reports of continuous CO measurements based on pulse transit time, which is inexpensive and easy to use but showed poor agreement with gold standard. Therefore, it would be advantageous to provide a device and method to estimate SV based on the PWV in patients undergoing cardiac surgery.

SUMMARY OF THE INVENTION

A device for measuring a ventricular-arterial coupling of a subject is disclosed. The device includes first and second inputs. The first input receives signals from a plurality of electrocardiogram sensors that are coupled to the subject at a plurality of first locations. The second input receives signals from a plurality of photoplethysmogram sensors that are coupled to the subject at a plurality of second locations. The second locations are selected from the group consisting of a head of the subject, an arm of the subject, and a leg of the subject. The signals received from the electrocardiogram sensors and the signals received from the photoplethysmogram sensors are received simultaneously. The device also includes a monitor configured to display the signals from the electrocardiogram sensors and the signals from the photoplethysmogram sensors. The device is configured to measure a time to arrival between a time at which an aortic valve of the subject opens to a pulse wave arrival at one or more of the second locations. The device is also configured to measure an ejection time, a delta ejection time, and an ejection time index of the subject. The device is configured to determine that the ejection time is different in different parts of a vascular tree of the subject based at least partially upon the delta ejection time and the ejection time index.

The device is also configured to measure a velocity of the pulse wave and to determine a distance that the pulse wave travels based at least partially upon the ejection time and the velocity of the pulse wave. The device determines the ventricular arterial coupling based on the comparison of the pulse wave travel distance and the measured vascular path length.

A method for measuring a ventricular-arterial coupling of a subject is also disclosed. The method includes receiving signals from a plurality of electrocardiogram sensors that are coupled to the subject at a plurality of first locations. The method also includes receiving signals from a plurality of photoplethysmogram sensors that are coupled to the subject at a plurality of second locations. The second locations are selected from the group consisting of a head of the subject, an arm of the subject, and a leg of the subject. The signals received from the electrocardiogram sensors and the signals received from the photoplethysmogram sensors are received simultaneously. The method also includes determining a time to arrival between a time at which an aortic valve of the subject opens to a pulse wave arrival at one or more of the second locations. The method further includes determining an ejection time, a delta ejection time, and an ejection time index of the subject. The device is configured to determine that the ejection time is different in different parts of a vascular tree of the subject based at least partially upon the delta ejection time and the ejection time index.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIGS. 9A, 9B, 9C, Toe-Finger: FIGS. 9D, 9E, 9F, Finger-Ear: FIGS. 9G, 9H, 9I).

FIGS. 13A-13G illustrate graphs showing subjects that have been divided into two groups according to their percentile rank of the ΔETToe-Finger in the supine position to investigate if ΔETToe-Finger may differentiate a more compliant from a less compliant vasculature similar to ΔΔETToe-Finger (FIG. 13A). Subjects in group 2 with a higher ΔETToe-Finger tended to be younger (30±10 years vs 36±5 years, P=0.11) (FIG. 13B), have lower MAPs (76±8 mmHg vs 81±9 mmHg, P=0.26) (FIG. 13E), and lower $PWV_{\Delta PAT\ Toe-Finger}$ (6.12±1.18 m/s vs 6.98±1.03 m/s, P=0.25) (FIG. 13F) compared to subjects in group 1 with a lower ΔETToe-Finger. In FIGS. 13C, 13D and 13G, BMI, HR, and $\Delta PWV_{\Delta PAT\ Toe-Finger}$ were not different between the group 1 and 2 (P=0.93, P=0.82, and P=0.99 respectively).

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

Figure 1:
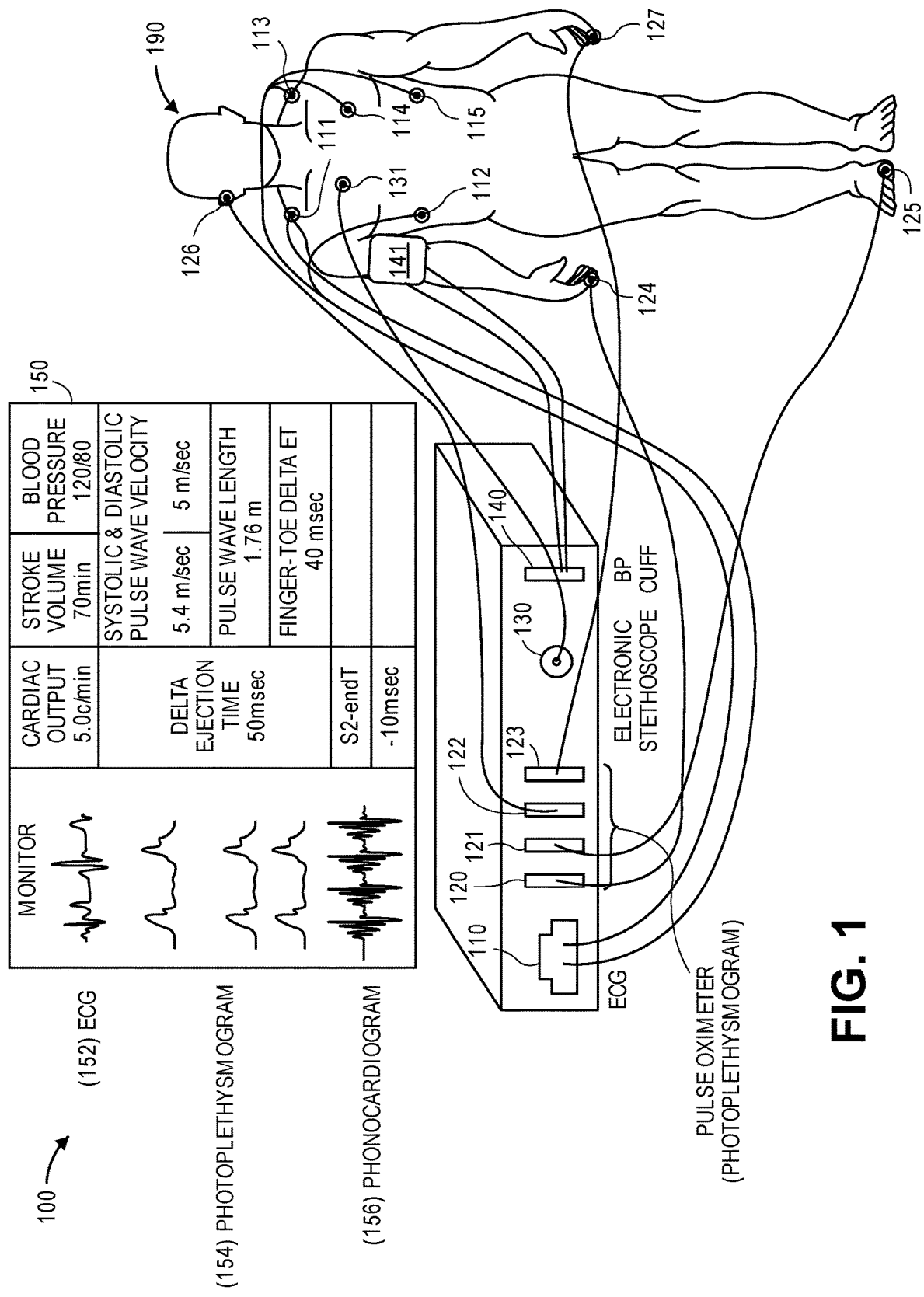
FIG. 1 illustrates a device for measuring an arterial vascular performance of a subject.

FIG. 1 illustrates a device 100 for measuring an arterial vascular performance of a subject 190. The device 100 may include one or more electrocardiogram (EKG, also known as ECG) inputs (one is shown: 110). The EKG input 110 may be configured to receive signals from one or more sensors (five are shown: 111-115) that are coupled to the subject 190. As shown, the sensors 111-115 may be coupled to the subject's chest, shoulders, torso, and/or back. The signals may be or include EKG signals (e.g., Q, R, S, T waves).

The device 100 may also include two or more pulse oximeter inputs (four are shown: 120-123) or any other sensors such as IR plethysmogram, laser flow, pressure, bio-impedance to derive arterial pulsations waveform. The inputs from such sensors 120-123 may be configured to receive signals from sensors (four are shown: 124-127) that are coupled to the subject 190. As shown, one of the sensors 124 may be coupled to the subject's arm (e.g., finger), one of the sensors 125 may be coupled to the subject's leg (e.g., toe), one of the sensors 126 may be coupled to the subject's head (e.g., ear), and one of the sensors 127 may be coupled to the subject's other arm (e.g., finger).

The signals provide the arterial pulse waveform. Thus, the signals include 1) the initial upstroke which corresponds to arrival of the pressure waveform and diastolic blood pressure; 2) the highest peak which corresponds to the systolic blood pressure; 3) another small peak and local nadir between the systolic peak and the second small peak called the dicrotic notch which corresponds to arrival of the pressure drop due to the aortic valve closure; and 4) the time difference between the initial upstroke and nadir which corresponds to the ejection time of the heart. The signals enable the user to calculate 1) the time of the pulse wave arrival from the heart to the site of sensor application (PAT time)—from the R peak of ECG or origin of $1^{st}$ heart sound on phonocardiogram to the initial upstroke on the pulse oximetry waveform; 2) the time of the pressure drop arrival due to the aortic valve closure—from the $2^{nd}$ heart sound origin on the phonocardiogram to the dicrotic notch on the pulse oximetry waveform; and 3) ejection times—the time difference between initial upstroke and nadir which corresponds to ejection time of the heart at different locations in the body and at different positions (e.g., standing, sitting, lying flat) for a single heartbeat.

The device 100 may also include one or more electronic stethoscope inputs (one is shown: 130). The electronic stethoscope input 130 may be configured to receive a signal from one or more sensors (one is shown: 131) that is coupled to the subject 190. As shown, the sensor 131 may be coupled to the subject's chest.

The device 100 may also include one or more blood pressure inputs (one is shown: 140). The blood pressure input 140 may be configured to receive a signal from one or more sensors (one is shown: 141) that is coupled to the subject 190. The sensor 141 may be or include a blood pressure cuff that is wrapped around the subject's arm, forearm, or fingers. The signal may be or include the subject's blood pressure.

The device 100 may also include a monitor 150 that is configured to display waveforms based upon the signals received. The waveforms may be or include an EKG waveform 152 (e.g., from the EKG input 110), a photoplethysmogram (PPG) waveform 154 (e.g., from the pulse oximeter inputs 120-123), and a phonocardiogram waveform 156 (e.g., from the electronic stethoscope input 130). The monitor 150 may also be configured to display the cardiac output, the stroke volume, the blood pressure, the ejection time, delta ejection time ΔET (i.e., the difference in ejection time between different locations in the body), ejection time index ΔΔET (i.e., the difference between ejection times between different locations and in different positions in the body), the PAT, the DAT, the systolic and diastolic pulse wave velocity, and the duration from the start of the second heartbeat (S2) to the end of the T wave from the EKG (end T), the electrical and electromechanical restitution curves (e.g., the duration of QT or QS2 interval as function of preceding TQ or S2Q intervals).

As described in greater detail below, the device 100 may be configured to measure a time to arrival. The time to arrival may be from a first time at which an aortic valve of the subject 190 opens to second time at which the pulse wave arrives at one or more of the locations where the photoplethysmogram sensors 120-123 are attached to the subject 190. The device 100 may also be configured to measure an ejection time, a delta ejection time, and an ejection time index of the subject 190. The device 100 is configured to determine that the ejection time is different in different parts of a vascular tree of the subject 190 based at least partially upon the delta ejection time and the ejection time index.

Figure 2:
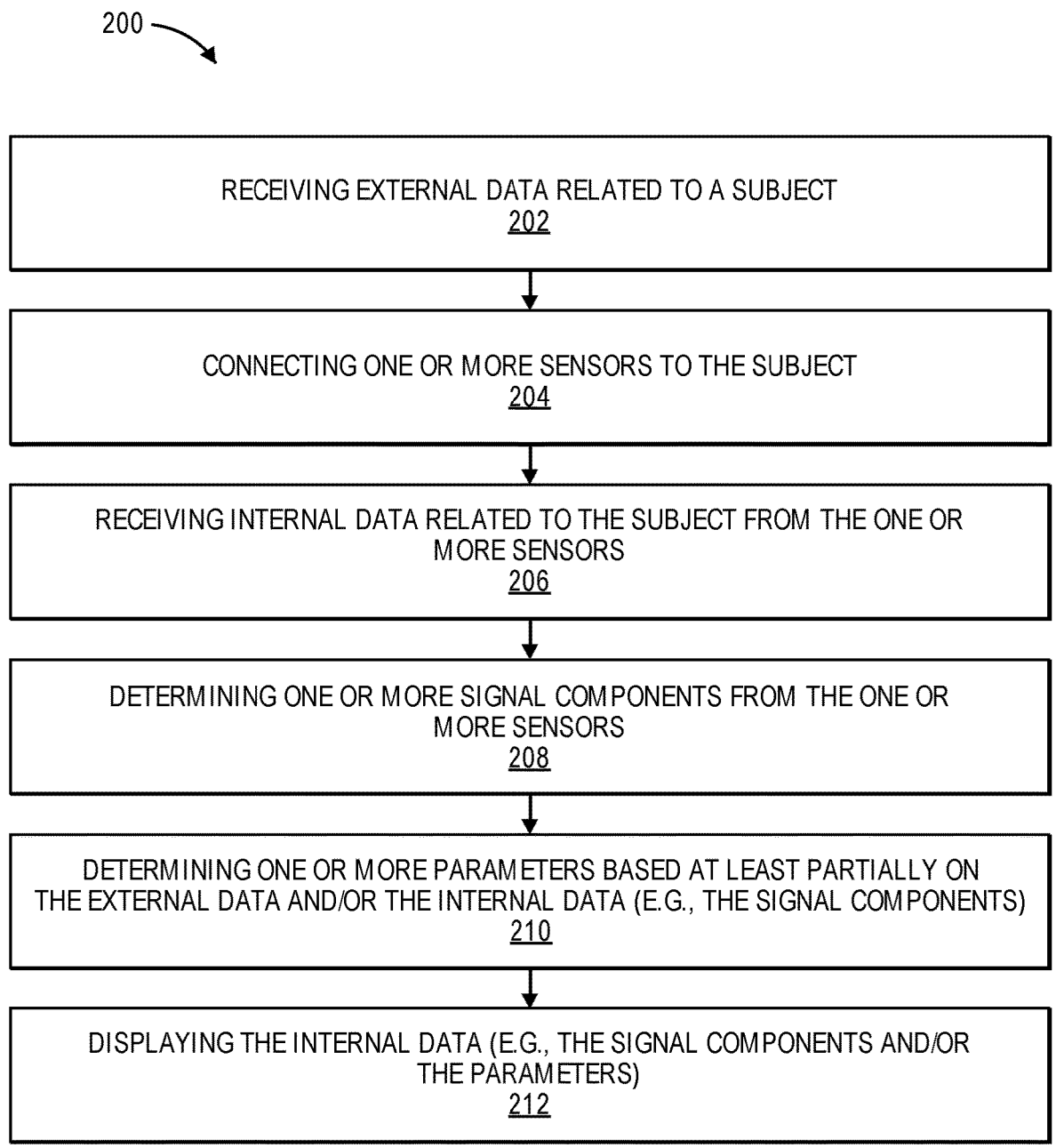
FIG. 2 illustrates a flowchart of a method for measuring an arterial vascular performance of a subject.

FIG. 2 illustrates a flowchart of a method 200 for measuring an arterial vascular performance and/or a ventricular-arterial coupling of a subject 190. The method 200 may use parameters such as ET, PAT (the ratio of ET/PAT and difference ET-PAT), pulse wave travel distance and its relationship to distance from the heart to the toe, ET difference between two peripheral locations (ΔET) and the difference between ΔET in the supine and standing positions (ΔΔET). ΔET may be a real-time, continuous, and non-invasive parameter of vascular properties, and the ΔΔET may be a non-invasive parameter of vascular reactivity.

The method 200 may include measuring/receiving external data related to the subject 190, as at 202. The external data may be or include anthropometric data. For example, the external data may be or include height, weight, demi-span, and/or the distance from the sternal notch to the index finger, ear lobe, and/or toe.

The method 200 may also include connecting one or more sensors 111-115, 124-127, 131, 141 to the subject 190, as at 204. The sensors may be or include the one or more EKG sensors 111-115 to the chest, shoulders, torso, and/or back, the one or more photoplethysmogram sensors 124-127 to the ears, fingers, and/or toes, the one or more electronic stethoscope sensors 131 to the chest wall in the second intercostal space on the right side or the $3^{rd}$ intercostal space on the left side along the sternal border, and the blood pressure sensor (e.g., cuff) 141 around the arm. The sensors 111-115, 124-127, 131, 141 may be non-invasive.

The method 200 may also include receiving internal data measured by the sensors 111-115, 124-127, 131, 141, as at 206. The internal data may be received in real-time. The internal data may be high temporal resolution (e.g., 1000-5000 measurements per second).

The method 200 may also include determining one or more signal components from the internal data, as at 208. The signal components from the EKG input 110 may be or include the origin and the peak and end of the P, Q, R, S, T, and U waves. The signal components from the photoplethysmogram inputs 121-123 may be or include the origin, the peak of the arrival wave, the dicrotic notch nadir and post dicrotic notch peak. The signal components from the stethoscope input 131 may be or include the phonocardiogram start of S1 and S2 heart sounds, the peak, and the end as well as pathological heart sounds (S3, S4) or heart murmurs from diseased heart valves.

The method 200 may also include determining one or more parameters based at least partially on the external data and/or the internal data (e.g., the signal components), as at 210. The parameters may be or include the heart rate, the blood pressure, the finger-toe PWV, the ear-toe PWV, and the ejection time at different locations and in different positions and Pulse Wave Transit Distance. The parameters may also include arterial tree volume (e.g., based on the external data), the stroke volume (e.g., based on the PWV), the cardiac output (which equals the stroke volume×heart rate), the difference in ejection time between different locations derived from the photoplethysmogram waveform 154, and the difference in time delay between the start of the second heart sound and the end of the T wave on the EKG. The parameters may also include a time to arrival of a pulse wave from a heartbeat of the subject to the photoplethysmogram sensors 124-127.

The method 200 may also include displaying the internal data, as at 212. This may include displaying the waveforms 152, 154, 156. In other embodiments, this may include displaying the signal components from the internal data. In yet other embodiments, this may include displaying the parameters.

An embodiment in accordance with the present invention provides analysis of a disturbed pattern of a pulse wave front. The analysis results in a non-invasive, real-time diagnostic tool of arterial vascular performance on both a global and regional scale. A novel, non-invasive, real-time monitoring device provides a single number describing how well the arterial tree as a whole is coupled to receive and distribute a stroke volume of a single heartbeat. Changing heart rate, contractility, volume status, afterload, and position of the patient will change the stroke volume, ejection time, and stroke volume distribution. Different vasculatures with different properties (e.g., size and intrinsic stiffness) may be best matched for different stroke volumes and ejection times to provide optimal coupling. The device will allow finding the optimal set of parameters for an individual patient.

The heart uses the arterial tree as a vehicle to deliver the stroke volume and energy associated with a single heartbeat to the microcirculation of peripheral tissues. In a healthy individual, the mean pressure decreases by only 1 to 2 mm Hg between the ascending aorta and a peripheral artery, indicating excellent ventricular arterial coupling with minimal energy loss in the arterial tree itself. To achieve such optimal coupling, the front of the pulse wave should arrive to the microcirculation of different tissues relatively simultaneously. If, in some portions of the vascular tree, pulse waveforms arrive sooner, microcirculation of these tissues may be exposed to pressure overload (e.g., brain and kidney in hypertension). In regions where the pulse waveforms arrive later, or do not arrive at all (e.g., post bypass vasoplegia with low stroke volume), the microcirculation will be under-perfused. To quantify the ventricular-vascular coupling time of the pulse wave front arrival to different peripheral sites of vasculature under different hemodynamic loads are to be measured. The present disclosure uses different noninvasive techniques of pulse arrival detection, such as pulse oxymetry, tonometry, bio-impedance coupled to an EKG, or other methods of detecting heart cycles, such as phonocardiogram, to measure the arrival of different portions of the pulse wave (e.g., front or dicrotic notch). The time difference between the soonest and slowest pulse wave arrival may be an indicator of coupling (e.g., small differences in the standing position may indicate good coupling and large differences indicating poor coupling. Similarly, small differences in the supine position may indicate poor coupling and large differences indicating good coupling). The time difference between the pulse arrival to a specific vascular bed and remaining heart contraction (=remaining ejection time) may be an indicator of vascular bed hyperperfusion and pressure overload. Similarly, if the ejection time is short, or the PWV is slow, the pulse may not arrive at the most distal vascular bed, leading to hypoperfusion. This may happen when the pulse arrival time is longer than ejection time.

The PWTD may have better predictive value than the PWV in regards to clinical outcomes. The reason for this is that for the same PWV, patients with a longer ET (and hence even longer PWTD) would expose their hearts and arterial tree to more pressure overload compared to patients with a lower ET. Similarly, tall subjects with a longer arterial tree can tolerate higher PWV values for the same ET without developing pressure overload compared to shorter individuals. Since heart rate is the main factor influencing ET, patients with higher PWV may develop less pressure overload with faster HR (shorter ET). Indeed, it has been shown both in animals and humans that higher PWV is associated with faster HR. Similarly, taller patients can tolerate lower heart rates. As PWV increases with changing position from supine to standing, ET decreases to keep steady state PWTD. As a result, normal coupling in healthy vasculature may be disrupted in elderly subjects with increased arterial stiffness, such that $PWTD_{Toe}$ is longer than $D_{Toe}$, the $ET_{Ear}/PAT_{Toe}$ ratio is more than 1, and $ET_{Ear}$-$PAT_{Toe}$ difference is positive. If $PWTD_{Toe}$ is longer than $D_{Toe}$, or if ET is longer than $PAT_{Toe}$, then higher pressures are generated and a higher augmentation pressure should be observed in the arterial system. Similarly, a slow PWV requires more time to fill the arterial tree and needs to be matched to a longer ET. If a slow PWV is matched to a shorter ET, then the most distant portions of the arterial tree may remain relatively under-filled (as in states of vasoplegia). Therefore, if PWTD is matched to arterial pathway distance, ET should be matched with the corresponding PAT.

Ejection time at the level of the heart can be estimated by QT, RT or QS2 intervals with current sensors. As the pulse wave generated by the heart ejection travels across the vasculature, it gets distorted. As a result, the ejection time measured at the peripheral site is different than at the central site. Compliant vasculature dampens stroke volume more and, as a result, prolongs the peripherally-measured ejection time. Stiff vasculature does not prolong the ejection time. The stiffness of the vasculature depends on its intrinsic properties but also on distention pressure. Hence, in the standing position, the distention pressure is higher in the lower extremities vasculature and lower in the head vasculature. At the arm, it undergoes minimal changes. The ejection time duration does not vary greatly in patients with intrinsically stiff vasculature that change position from the supine position to the standing position. However, patients with intrinsically compliant vasculature lying flat greatly prolong the ejection time compared to the standing position. This change in ejection time duration with changing positions is a novel non-invasive marker of vascular health. To account for the changes in central ejection time, measuring the delta-delta ejection time is proposed (e.g., the difference between ejection times between two peripheral locations e.g., finger and toe in supine vs standing positions).

The pulse wave velocity and ejection time may be measured simultaneously. The pulse wave travel distance (PWTD) may be calculated using the pulse wave velocity and ejection time (e.g., PWV in meters/second*ET in seconds). The pulse wave travel distance is basically the distance the pulse travels in the vasculature during a single heartbeat. When the heart ejection is coupled to the vasculature, the stroke volume fills the arterial tree without over-distention or under-distention. This is achieved when the PWTD is coupled to the patient height/distance from the heart to the peripheral tissue beds. In cases when the vasculature is stiff or blood pressure is high, the PWV is high. If the heart rate is slow (e.g., due to beta blockers), the ejection time is long. As a result, the PWTD may greatly exceed the patient height/vascular path length, meaning the stroke volume exceeds the capacity of vasculature to accommodate it. This means that the vasculature would be exposed to extra pressure and volume, and the heart would be exposed to extra resistance from overly distended vasculature (e.g., poor coupling). If the PWV is low (e.g., due to low blood pressure), and the ejection time is low (e.g., hypovolemia and high heart rate), then the PWL may be less than the patient height/vasculature length, and poor coupling will occur, meaning the stroke volume is significantly less than the capacity of vasculature to accommodate it. Optimal hemodynamics (e.g., BP, HR, vascular tone) may result in such combinations of PWV and ejection time that the PWTD is close to the patient distance to the most distal site in the vasculature (toe).

The architecture of a normal arterial tree is elegant for its conduit and cushioning functions. The arterial tree receives blood in pulses of stroke volume from the heart. Each pulse is then spread across the arterial tree in a centrifugal manner from the heart to microcirculation in peripheral tissues. It is in the best interest of the organism to deliver blood to the tissues with minimal energy expenditure and time delay. The actual blood flow in the arterial tree is not constant but rather pulsatile, despite the cushioning effect mediated by the elastic nature of the vasculature. Most of blood flow happens at the front of pulse wave during systole. The pulse travels along the arterial tree with a specific speed: the pulse wave velocity. Experimental evidence suggests that this speed is constantly changing in different portions of the vascular tree even in healthy subjects. It is believed that it is due to strong dependence of the pulse wave velocity on the size of the artery and wall tension, the smaller the artery, the higher the pulse wave velocity. As a result, the pulse wave accelerates as it spreads from the heart to the periphery. It is counterintuitive, but the best analogy is the recently discovered accelerating expansion of the universe. Astrophysicists have known for a long time that the universe is expanding, but they believed that the expansion was slowing down. It is, however, now established that the expansion is indeed accelerating. Similarly, the blood ejected by the heart engages the arterial tree with the accelerating pulse wave velocity as it reaches peripheral tissues even as the average velocity of blood flow in microcirculation is slowing and becomes virtually non-pulsatile. The front of the pulse wave spread may have a unique shape/pattern in a 3D structure of the vascular tree depending on regional PWVs. In healthy vasculature nicely coupled to the heart, the front of the pulse wave arrives to the microcirculation of different tissues relatively at the same time in standing position, ensuring that pressure gradients between areas where the pulse has already arrived (high systolic pressure) and areas with delayed arrival of pulse (low diastolic pressure) are minimal. This ensures the most efficient vascular function of blood and energy transfer. Changing position may change distending pressure within the artery and, as such, its wall tension. Because pulse wave velocity depends not only on arterial size but also on wall tension, changes in position may lead to changes in the shape of the pulse wave front unless compensated for by changes in vascular size due to vascular reactivity. Exercise will increase both stroke volume and blood pressure, and, as such, it will increase the arterial wall tension. Since pulse wave velocity depends not only on arterial size but also on wall tension, hemodynamic changes (e.g., elevation in blood pressure) elicited by exercise may lead to changes in the shape of the pulse wave front and, hence, lead to different time arrival of pulses to different peripheral tissues.

The heart does not work independently, but rather is coupled in a closely orchestrated manner with the vasculature. The properties of the arterial vascular tree exert an enormous effect on the heart function. In addition, a properly functioning vasculature delivers blood and energy from the heart to peripheral tissues in a most efficient way, without imposing extra resistance and energy loss. Investigating ventricular-vascular coupling requires invasive and highly sophisticated technology (e.g., PV loops), which are rarely done in the clinical setting. To quantify vascular health, central pulse wave velocity measurements have been used. These measurements are neither real-time nor continuous, as they are difficult to perform and time-consuming. The proposed device may expand the current understanding of vascular function and bring a new layer of knowledge to the fundamentals of blood transfer from the heart to the peripheral tissues. The proposed method and device hold significant potential for the development of non-invasive, real-time technology to assess global arterial vascular function by assessing the pattern of pulse wave fronts from each heartbeat and how it changes with changes in position, which provides different hydrostatic pressure loads to different portions of the vascular tree. Since measurements are based on routine non-invasive clinical tools (e.g., pulse oximetry and EKG), the device and method can be easily incorporated into clinical settings including operating rooms and critical care units—sites in which optimizing ventricular-vascular coupling might be crucial. The described technology may be easily applied to a cardiovascular patient population. Many patients are elderly with non-compliant stiff vasculature and/or impaired ventricular-arterial coupling. Pulse wave velocity is greatly increased in such patients with stiff central vasculature, and that will have a dramatic impact on the pulse wave front. The smaller the effect that orthostatic changes exert on the pulse wave front, the more intrinsic vascular stiffness is present from elevated blood pressure or arteriosclerosis. In such patients, the pulse wave front may arrive sooner to the proximal organs such as the brain and kidney compared to the arms and legs and will result in a pressure overload of the brain or kidney microcirculation. This can be measured by the difference from the pulse arrival to the head and remaining central ejection time (e.g., start of S2 or end of T). If the stroke volume is low and ejection time is short, then the pulse wave front might not arrive in the distal portions of the body (e.g., fingers and toes) at all, making those tissues hypo-perfused. In patients with peripheral vascular disease, significant obstruction of a particular artery will cause delay in the pressure wave front arrival downstream of an obstruction due to loss of distending pressure.

As such, analysis of the disturbed pattern of the pulse wave front may provide a non-invasive, real-time diagnostic tool of arterial vascular performance on both a global and regional scale. A non-invasive, real-time monitoring device providing a single number of how well the arterial tree as a whole is coupled to receive and distribute a stroke volume of a single heartbeat is also provided with the present invention. Changing heart rate, contractility, volume status, and afterload may change stroke volume and ejection time. Different vasculatures with different properties (e.g., size and intrinsic stiffness) may be best matched for different stroke volumes and ejection times to provide optimal coupling. The device will allow finding the optimal set of parameters for an individual patient. In addition, it can provide an optimal set of parameters for end organ perfusion (e.g., head) in individual patients.

Figure 3:
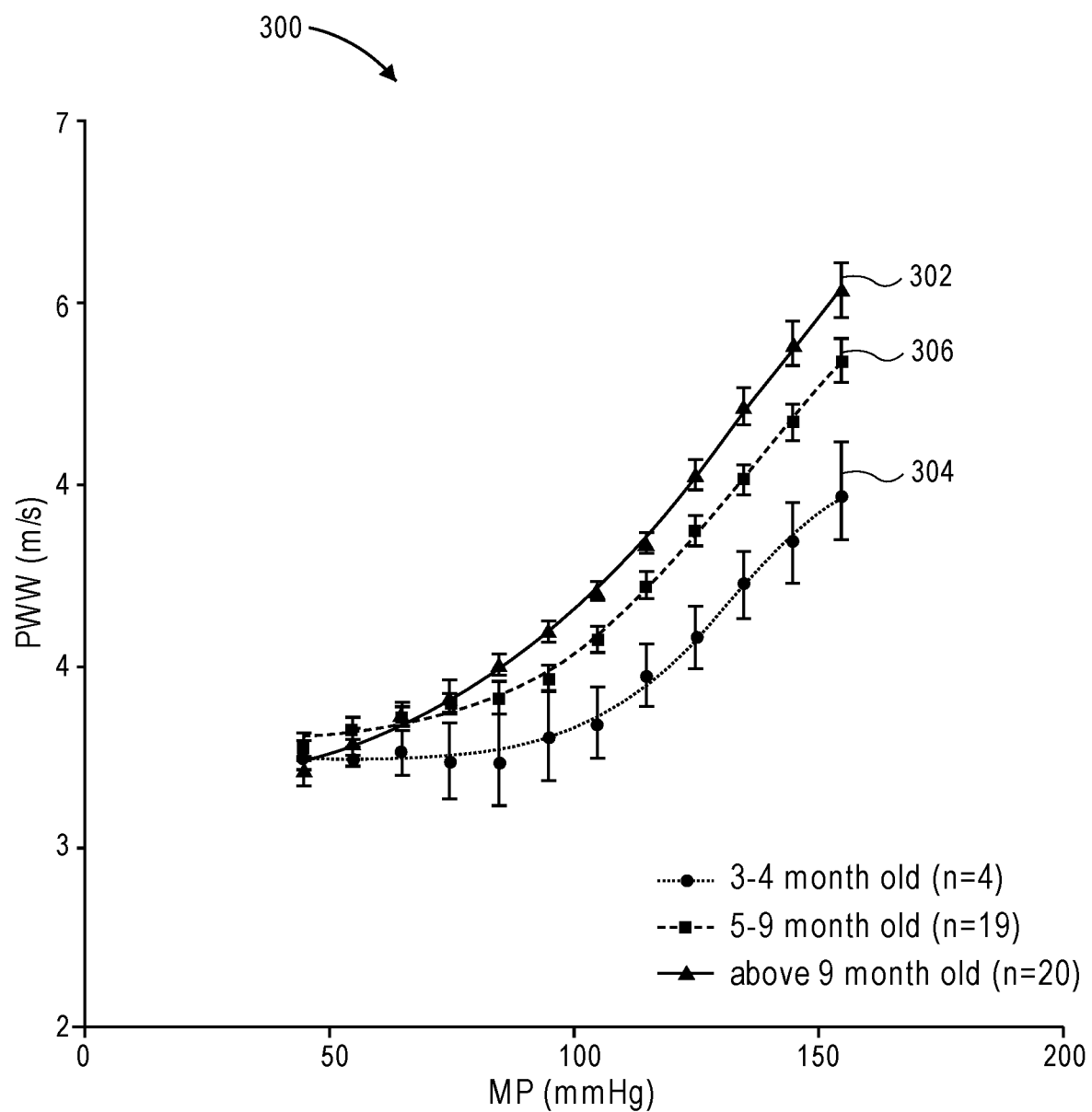
FIG. 3 illustrates a graphical view that shows that a central aortic PWV is not constant, and it is dependent both on blood pressure as well as age of vasculature.

The pulse wave front spreads according to PWV. FIG. 3 illustrates a graph 300 showing that central aortic PWV is not constant, and it is dependent both on blood pressure as well as age of vasculature. Line 302 is an old vasculature, line 304 is a young vasculature, and line 306 is a middle-aged vasculature. As such, for a particular patient with a particular hemodynamic state, the PWV and resultant pulse wave front may be different.

To assess this, an exemplary implementation of the present invention will measure the time to arrival of the pulse wave at different locations in the body for a single heartbeat. To achieve this, several pulse detection probes (e.g., adult pulse oximeter probes) may be simultaneously used and placed at different peripheral parts of body (e.g., fingers of left and right arms, fingers of left and right legs, ears, nose, or lip). The analog pulse detection signals may be digitized to determine the precise time measurements of pulse arrival between different sites for the same heartbeat. The pulse travel time may be precisely timed against the EKG signal (e.g., R wave). To assess the vascular performance in different positions, measurements will be performed while subjects are supine, sitting, standing, or in the head-down position. To assess the vascular performance during exercise or stress testing, measurements will be performed before and after mild-moderate exercise (e.g., 30 knee-bends) or during standardized cardiovascular stress testing. The arrival times may be measured and recorded in real-time electronically.

The time delay between the fastest and slowest to arrive, adjusted for heartrate, is a measure of the efficiency of coupling. The time difference in the pulse wave front arrival between the earliest and latest to arrive will provide the index of coupling. The time difference between pulse arrival to specific vascular bed and remaining heart contraction (=remaining ejection time) will be indicator of the particular vascular bed hyperperfusion and pressure overload. Similarly, if ejection time is short or PWV is slow, the pulse might never arrive to the most distal vascular bed, leading to hypoperfusion. This may happen when the pulse arrival time is longer than the ejection time.

In healthy individuals that are free from vascular disease (representing normal physiological conditions), the pulse wave arrives relatively simultaneous to all peripheral tissues despite dramatic changes in path length. Non-simultaneous pulse arrival may lead to the development of pressure gradients between different portions of the arterial tree. Because the arterial tree does not have valves, it may theoretically lead to a "steal phenomenon," where blood from arterial beds with higher pressure (e.g., systolic) flows to another arterial bed with a lower pressure (e.g., diastolic) down a pressure gradient. To put this into perspective, the relative distance from the heart to the ear is 3.3 times shorter than that from the heart to the finger, and 5.7 times shorter compared to the toe, as shown in Table 1 below. If pulse wave velocity is constant across different paths, then one could expect the pulse arrival will be around 3.3 times longer to the finger and 5.7 times longer to the toe, compared to the ear.

properties (e.g., size and intrinsic stiffness) may be best matched for different stroke volumes and ejection times to provide optimal coupling. The device find the optimal set of parameters for individual patient. The time difference between the pulse arrival to specific vascular bed and remaining heart contraction (=remaining ejection time) may be indicator of vascular bed hyperperfusion and pressure overload. Similarly, if the ejection time is short or PWV is slow, the pulse may not arrive to the most distal vascular bed, leading to hypoperfusion. This may happen when the pulse arrival time is longer than ejection time.

13 healthy volunteers, with no history of vascular or cardiac disease, age 23-41 years old, participated in the study. Inclusion criteria were: Healthy adults of ages 21-50 years, both genders. Exclusion criteria were: Subject refusal to participate, known cardiovascular disease, ages <21 or >50 years, pregnancy, and any disability preventing mild physical exertion. Two subjects who joined the study were excluded. The first was excluded due to inability to finish the study protocol. The second was excluded due to being unable to produce a readable plethysmograph signal on her toes. After verifying that the remaining subjects had no restrictions to participate in the study, each subject's weight, half wingspan (i.e., the distance from the sternal notch to the index finger with the arm in 90 degree lateral extension), and self-reported height were recorded.

A standard 3 lead EKG was placed on the subjects for the continuous monitoring of electrical cardiac activity. First, capillary plethysmograph sensors were placed on both left and right sides for each of the following locations: ear lobes

TABLE 1

Cohort demographics and baseline characteristics

| Subject | Weight (kg) | Height (kg) | Length Ratio | | | Systolic BP (mmHg) | Diastolic BP (mmHg) | Age (years) | Gender |
|---|---|---|---|---|---|---|---|---|---|
| | | | Toe:Ear | Toe:Finger | Finger:Ear | | | | |
| 1 | 80.5 | 188.0 | 5.9 | 1.8 | 3.4 | 113 | 64 | 23 | M |
| 2 | 57.5 | 162.6 | 5.6 | 1.7 | 3.4 | 108 | 68 | 36 | F |
| 3 | 63 | 174.0 | 6.0 | 1.9 | 3.2 | 110 | 63 | 26 | F |
| 4 | 95.5 | 177.0 | 5.8 | 1.8 | 3.3 | 142 | 84 | 39 | M |
| 5 | 54.2 | 164.0 | 5.5 | 1.7 | 3.2 | 111 | 67 | 36 | F |
| 6 | 79.5 | 175.3 | 5.7 | 1.7 | 3.4 | 116 | 62 | 31 | M |
| 7 | 82.1 | 174.0 | 5.7 | 1.7 | 3.3 | 113 | 64 | 41 | M |
| 8 | 47.7 | 165.0 | 5.5 | 1.7 | 3.3 | 98 | 61 | 23 | F |
| 9 | 60.1 | 171.0 | 5.6 | 1.7 | 3.3 | 95 | 58 | 23 | F |
| 10 | 69.5 | 172.7 | 5.7 | 1.7 | 3.3 | 117 | 69 | 29 | M |
| 11 | 94.6 | 177.8 | 5.8 | 1.7 | 3.4 | 128 | 68 | 26 | M |
| Mean | 71.3 | 172.8 | 5.7 | 1.7 | 3.3 | 114 | 66 | 30.3 | |

Exercise and postural change affect pulse wave velocity through the vasodilation of arterioles supplying active muscles and increased vasoconstriction due to sympathetic stimulation. Hence, these factors may also significantly affect pulse arrival times at different peripheral vascular beds. Similar to basal conditions, pulse arrival time to different peripheral vascular beds may be relatively simultaneous after exercise and with postural changes.

Analysis of a disturbed pattern of the pulse wave front may provide a non-invasive, real-time diagnostic tool of arterial vascular performance on both a global and regional scale. A non-invasive, real-time monitoring device may provide a single number describing how well the arterial tree as a whole is coupled to receive and distribute a stroke volume of a single heartbeat. Changing heart rate, contractility, volume status, and afterload may change stroke volume and ejection time. Different vasculatures with different in a standing position, index fingers in a sitting position with hands hanging free by their sides, and on the big toes lying in a supine position. EKG and plethysmograph were simultaneously recorded bilaterally for each location (i.e., ears, index finger, big toe). Then, 3 lead EKG signals were recorded along with plethysmographs from one unilateral ear, finger, and big toe for 30 seconds in the standing, sitting, and supine positions. The EKG and plethysmograph sensors were then removed from the subjects, and a blood pressure cuff was then applied to the subjects to record blood pressure in the standing, sitting, and prone positions, respectively. For the exercise part of the experiment, subjects were then required to perform 30 squats. EKG and plethysmograph sensors were then reattached to subjects' unilateral ear lobe, index finger, and big toe, and recording was redone in the standing, sitting, and supine positions as described above. All data for the 'post exercise' portion was collected within 3 minutes of the subject completing 30 squats. A Powerlab analog to digital converter and Labchart 8.0 software developed by Ad Instruments Ltd, Australia were used to convert and digitally record the EKG and plethysmograph signals.

From the data collected, the pulse arrival time (PAT) to each location (e.g., ear lobe, index finger, and big toe) was assessed by calculating the time delay between 2 characteristic spots: (1) the peak of the R wave on the EKG and (2) the first subsequent positive inflection on the plethysmograph trace. To compare pulse wave arrival times to different tissue beds from the same heartbeat, the corresponding R wave was taken on the EKG as a starting point where time was assigned to be zero.

Figure 4:
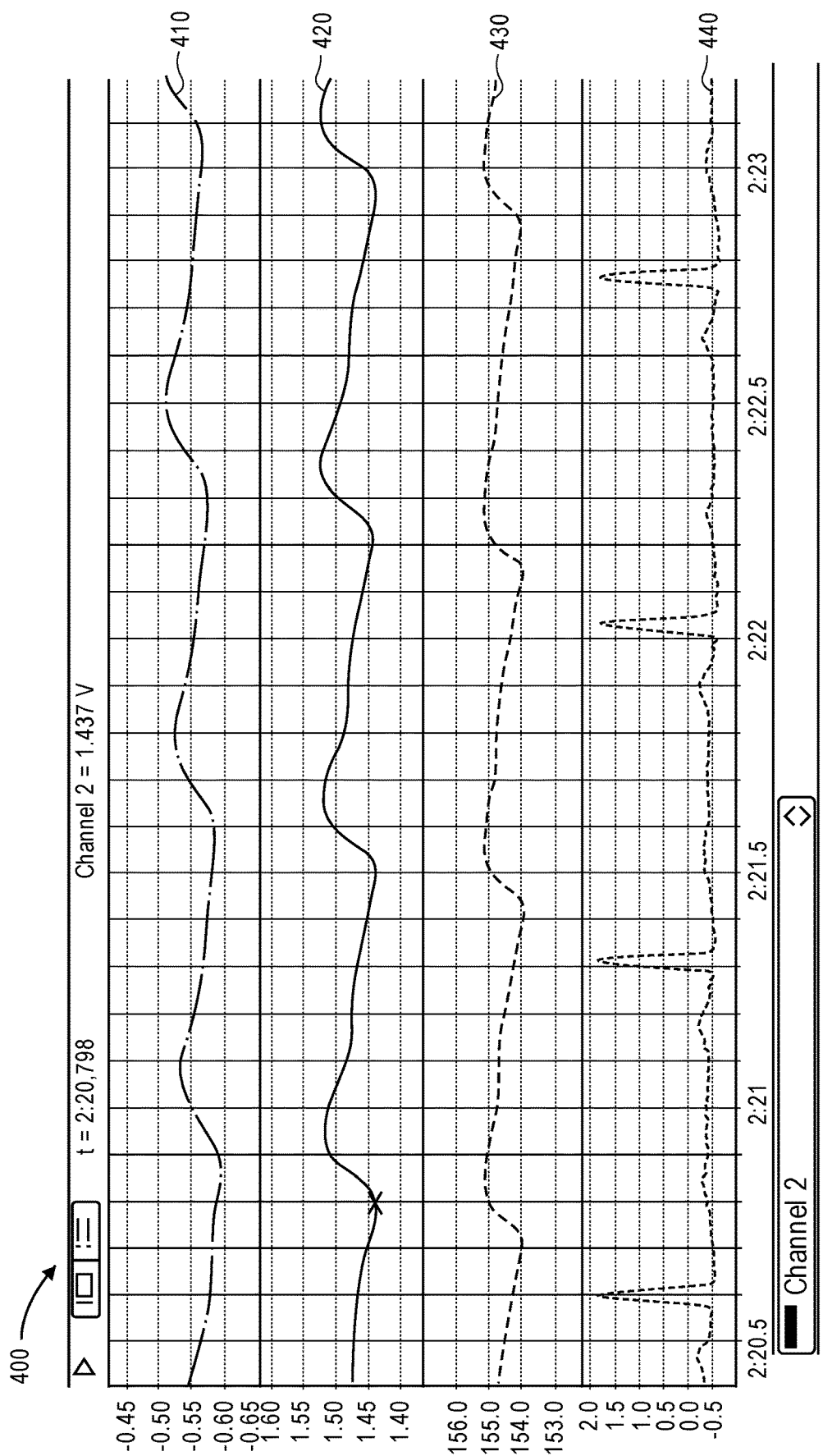
FIG. 4 illustrates a graphical view that shows an example of data presented in Labchart. Periods consisting of 10 consecutive heart beats from different positions (e.g., standing, sitting, supine) before and after exercise were then used to calculated the mean pulse arrival time (PAT), diastolic arrival time (DAT), and ejection time (ET) for the 3 locations: one for the head (e.g., ear lobe), one for the upper extremity (e.g., index finger), and one for the lower extremity (e.g., big toe). Usually, PAT are equal between the left side and the right side (e.g., left and right arm); however, more than 3 sensors can placed to increase accuracy (e.g., one on each side).

FIG. 4 shows graphs of three plethysmogram waveforms: the toe 410, the finger 420, and the ear 430, and a graph 440 of the EKG output. Periods consisting of 10 consecutive heart beats from each position (e.g., standing, sitting, supine) before and after exercise were then used to calculated the mean PAT for the 3 locations (e.g., ear lobe, index finger, big toe). To compare the relative time difference between the PAT to ear, finger, and toe, the ratio between the PAT was compared to corresponding locations. The collected data was then tabulated and used for statistical analysis.

Data was analyzed using STATA 12 software (StataCorp, College Station, Tex.). PATs are reported as mean+/−standard deviation. A paired t test was used to compare PAT between different locations before and after exercise as well as PAT ratios between different locations. The threshold for statistical significance was chosen to be $P<0.05$.

Demographics and baseline characteristics of volunteers are presented in Table 1. The average age was 30 years old and ranged from 23 to 41 years old. Females made up 45% of the cohort, and males were 55%. Mean systolic blood pressure was 114 mmHg, and mean diastolic blood pressure was 66 mHg at rest. The average length ratio for toe/ear was 5.7, finger/ear 3.3, toe/finger 1.7. Pulse arrival times from the peak of R wave on the EKG to arrival of the pulse wave are presented for each individual in supplement (1) at rest and (2) post exercise.

These times allowed us to assess the order in which the pulses arrived to different locations. In all subjects, at all positions both at rest and post exercise, the pulse arrival times from shortest to longest were as follows: ear lobe, index finger, and big toe, as shown in Tables 2 and 3, as expected from path length being shortest for the ear lobe and longest for the toe.

PATs to each location (e.g., ears, toes, fingers) were equal for the left and right side. As such, only one side (e.g., either left or right) was compared to measure the PATs at different locations. Table 2 presents data on the effect of exercise. The post-exercise mean PATs at all 3 locations in all 3 positions were shorter compared to at-rest PAT. However, it was not statistically significant for all positions and locations. Table 3 presents the mean PAT for all three positions at-rest and post-exercise.

TABLE 2

Effect of Exercise on Cohort Mean PAT of All Three Positions

|  | At rest | Exercise | P-Value |
| --- | --- | --- | --- |
| Standing |  |  |  |
| Ear | 0.15 ± 0.02 | 0.12 ± 0.01 | <0.001 |
| Finger | 0.21 ± 0.02 | 0.19 ± 0.03 | 0.26 |
| Toe | 0.26 ± 0.02 | 0.25 ± 0.02 | 0.27 |
| Sitting |  |  |  |
| Ear | 0.14 ± 0.02 | 0.12 ± 0.01 | 0.03 |
| Finger | 0.20 ± 0.01 | 0.18 ± 0.01 | <0.001 |
| Toe | 0.26 ± 0.02 | 0.25 ± 0.01 | 0.03 |
| Supine |  |  |  |
| Ear | 0.12 ± 0.02 | 0.11 ± 0.01 | 0.37 |
| Finger | 0.20 ± 0.01 | 0.18 ± 0.01 | 0.02 |
| Toe | 0.29 ± 0.02 | 0.29 ± 0.02 | 0.70 |

TABLE 3

Effect of Different Positions on Cohort Mean PAT at Rest and Post Exercise

| | At rest analysis (mean PAT ± s.d.) | | | | Post exercise analysis (mean PAT ± s.d.) | | | |
| --- | --- | --- | --- | --- | --- | --- | --- | --- |
| | Mean ear (s) | Mean finger (s) | Mean toe (s) | P-Value | Mean ear (s) | Mean finger (s) | Mean toe (s) | P-Value |
| Standing | 0.13 ± 0.02 | 0.20 ± 0.03 | | <0.001 | 0.12 ± 0.01 | 0.19 ± 0.03 | | <0.001 |
| | 0.13 ± 0.02 | | 0.26 ± 0.02 | <0.001 | 0.12 ± 0.02 | | 0.25 ± 0.02 | <0.001 |
| | | 0.20 ± 0.03 | 0.26 ± 0.02 | <0.001 | | 0.19 ± 0.03 | 0.25 ± 0.02 | <0.001 |

| | Mean ear (s) | Mean finger (s) | Mean toe (s) | P | Mean ear (s) | Mean finger (s) | Mean toe (s) | P-Value |
| --- | --- | --- | --- | --- | --- | --- | --- | --- |
| Sitting | 0.13 ± 0.02 | 0.19 ± 0.01 | | <0.001 | 0.12 ± 0.01 | 0.18 ± 0.01 | | <0.001 |
| | 0.13 ± 0.02 | | 0.26 ± 0.02 | <0.001 | 0.12 ± 0.01 | | 0.25 ± 0.01 | <0.001 |
| | | 0.19 ± 0.01 | 0.26 ± 0.02 | <0.001 | | 0.18 ± 0.01 | 0.25 ± 0.01 | <0.001 |
| Supine | 0.12 ± 0.02 | 0.19 ± 0.01 | | <0.001 | 0.11 ± 0.01 | 0.18 ± 0.01 | | <0.001 |
| | 0.12 ± 0.02 | | 0.29 ± 0.02 | <0.001 | 0.11 ± 0.01 | | 0.29 ± 0.02 | <0.001 |
| | | 0.19 ± 0.01 | 0.29 ± 0.02 | <0.001 | | 0.18 ± 0.01 | 0.29 ± 0.02 | <0.001 |

Effects of position and exercise on pulse arrival at the toe are now described. At rest, the longest time taken for pulse arrival to the toe was in the supine position (0.2911 s+/−0.0225) compared to the standing (0.2643 s+/−0.0181, p=0.006) and sitting positions (0.2634 s+/−0.0193, p=0.006). Similarly, during exercise, the longest PAT was seen in the supine position (0.2872 s+/−0.0232) compared to the standing (0.2541 s+/−0.0235, p=0.003) and sitting (0.2472 s+/−0.0137, p<0.001) positions.

Effects of position and exercise on pulse arrival at the index finger are now described. The effect of position on pulse arrival to the index finger was minimal compared to the toe or ear lobe. At rest, the longest time for pulse arrival to the index finger was in the standing position (0.2063 s+/−0.0154) compared to the sitting (0.1987 s+/−0.0112, p=0.12) and supine positions (0.1975 s+/−0.0096, p=0.79). A shorter PAT was seen after exercise, although, similar to rest conditions, the longest PAT occurred in the standing position (0.1940 s+/−0.0316) compared to the sitting (0.1799 s+/−0.1118, p=0.32) and supine (0.1833 s+/−0.0146, p=0.54) positions.

Effects of position and exercise on pulse arrival at the ear are now described. Compared to the toe and finger, the pulse wave always arrived to the ear first at all positions both at rest and post-exercise (see Table 2 and 3). At rest, the longest time for pulse arrival to the ear was in the standing position (0.1452 s+/−0.0162) compared to the sitting (0.1351 s+/−0.0191, p=0.20) and supine positions (0.1182 s+/−0.0158, p<0.001). Similarly, during exercise, the longest PAT was seen in the standing position (0.1213 s+/−0.0115) compared to the sitting (0.1184 s+/−0.0147, p=0.61) and supine (0.1131 s+/−0.0094, p=0.08) p<0.001 positions.

To present relative time delay between corresponding locations, the PAT ratios between toe/ear, toe/finger, and finger/ear were calculated and are presented in Table 4. The PAT ratio differences between locations were much smaller compared to the length ratio difference (finger/ear=3.3 and toe/ear=5.7).

1.38+/−0.06, and 1.57+/−0.16, respectively) were higher than the at rest ratios in all positions, but were not statistically significant.

The effect of position and exercise on the mean finger/ear PAT ratio ranges from (1.43+/−0.11) in the standing position at rest to (1.69+/−0.21) in the supine position at rest, which is much shorter than the expected range of 3.3 based on path length ratios. Changes in position and exercise made minimal effect on the ratios. The mean PAT ratio increased going from standing (1.43+/−0.11) to sitting (1.49+/−0.19) to supine (1.69+/−0.21). After exercise, no clear pattern in PAT ratio changes was seen due to positional change: it was shortest at the sitting position (1.53+/−0.15) followed by the standing (1.60+/−0.23) and supine positions (1.63+/−0.15), respectively, but these differences were not statistically significant. Post-exercise PATs were longer compared to at-rest PATs for the standing (1.60+/−0.23 vs. 1.43+/−0.11, p=0.03) and sitting (1.53+/−0.15, p=0.59) positions. The post-exercise PAT was shorter than the at-rest PAT in the supine position (1.63+/−0.15 vs 1.69+/−0.21, p=0.39).

The current study was performed on young, healthy individuals to investigate the physiologic mechanisms of pulse wave distribution across a healthy, compliant arterial tree. Using noninvasive methods, the pattern of pulse wave arrival was measured at three peripheral vascular beds at various positions and exercise statuses in healthy, young volunteers. The arterial tree allows the blood to be transported from the heart to peripheral tissue beds to supply tissue metabolic demands and maintain homeostasis. Blood

TABLE 4

Summary of Cohort Mean PAT Ratios at Rest and Post Exercise for All Positions

| PAT ratio | Standing | | | Sitting | | | Supine | | |
|---|---|---|---|---|---|---|---|---|---|
| | Toe/Ear | Toe/Finger | Finger/Ear | Toe/Ear | Toe/Finger | Finger/Ear | Toe/Ear | Toe/Finger | Finger/Ear |
| At rest | 1.8202 | 1.2811 | 1.4207 | 1.9496 | 1.3256 | 1.4707 | 2.4627 | 1.4739 | 1.6708 |
| Post Exercise | 2.0948 | 1.3097 | 1.5993 | 2.0878 | 1.3740 | 1.5194 | 2.5393 | 1.5668 | 1.6206 |

The effect of position and exercise on the mean toe/tar PAT ratio, depending on the position and exercise, ranges from 1.84+/−0.20 in the standing position at rest to 2.55+/−0.08 in the supine position post-exercise, which is less than half the mean path length ratio of 5.7. The mean PAT ratio increased, going from standing (1.84+/−0.20) to sitting (1.98+/−0.27) to supine (2.49+/−0.32), meaning that relative to the ear, the PAT at the toe is longest in the supine position and shortest in the standing position. The mean post-exercise ratios for standing, sitting, and supine positions (2.10+/−0.19, 2.11+/−0.20, and 2.55+/−0.08, respectively) were also higher than at-rest ratios (1.84+/−0.20, 1.98+/−0.27, and 2.49+/−0.10, respectively), although not all of these differences were statistically significant.

The effect of position and exercise on the mean toe/finger PAT ratio ranges from 1.28+/−0.10 (standing) to 1.57+/−0.16 (supine), which are smaller values than the expected ratio of 1.7. Changes in position and exercise were not always statistically significant. The mean PAT ratio increased going from standing (1.28+/−0.10) to sitting (1.33+/−0.11) to supine (1.47+/−0.10), but the differences between standing and sitting were not statistically significant both at rest and post-exercise. The mean post-exercise ratios in the standing, sitting, and supine positions (1.32+/−0.13, flow from the heart to the arterial system is provided in a pulsatile manner across the arterial system up to the pre-sphincter arterioles. This pulsatile waveform can be detected at peripheral tissues by devices and techniques such as plethysmography or pulse oximetry. The time taken for the pulse wave to reach the vasculature of various peripheral tissue beds depends on pulse wave velocity in each portion of the vascular tree and path length. The length of a particular vascular pathway remains relatively constant; however, the pulse wave velocity may undergo significant changes in particular arterial segments due to factors such as vascular tone and distending pressure changes. Because the arterial system does not have valves, changes in position such as from lying to standing may cause blood to pool in the lower extremities due to the formation of a hydrostatic gradient from head to toe. In reality, in healthy individuals, the body produces a myogenic response, reacting to this change in hydrostatic pressure by increasing the vascular tone and vasoconstriction in the lower extremities, leading to an increased distending pressure and wall tension in the arteries. This increase in wall tension contributes towards an increased PWV and hence a shorter PAT.

In the present invention, the effect of posture and exercise on pulse wave arrival time to different peripheral tissue beds was studied. The real-time, non-invasive technique of tissue plethysmography was used to detect the pulsatile waveform from which the pulse arrival was deduced. The effect of exercise on pulse arrival time was also explored. A shorter PAT is expected, because exercise causes an increase in the force of contraction, cardiac output, wall tension, and central arterial wall stiffness. Indeed, the findings showed that PAT across all locations were shorter post-exercise.

However, the pulse wave arrived relatively later to the lower extremities compared to fingers and ears as evidenced by the decreasing ratio of toe/ear PAT after exercise as compared to rest. One potential explanation is vasodilation in the metabolically active lower limbs and vasoconstriction in the less metabolically active upper limbs and head as the body optimized metabolic/perfusion matching. As the exercise subjects' performed squats, mainly utilizing muscles in the lower body, metabolic demand in the lower limb muscles would be higher than both the head and upper limbs. The net effect from the vasodilation in the lower limbs and vasoconstriction in the head and upper limbs was an increase in toe/ear PAT ratios seen post-exercise. This is consistent with the fact that an increase in vascular tone (e.g., vasoconstriction) would increase PWV, causing a decrease in PAT and vice versa.

The observations showed that a change in position from horizontal to vertical (e.g., supine to sitting to standing) led to a decrease in PAT to the toe and an increase in PAT to the ear. This might be explained by an increase in hydrostatic pressure in the arteries of lower extremities and a decrease in hydrostatic pressure in the arteries of the head and neck caused by the positional change from horizontal to vertical.

In healthy individuals, the vasculature adapts to the increase in hydrostatic pressure in the lower limbs by increasing wall tension stiffness. Without this response, blood would pool at the lower limbs, and the perfusion of the upper limbs and head would be reduced. Indeed, in many patients with orthostatic hypotension, disorders of the autonomic nervous system prevent this response from occurring, leading to reduced perfusion of the cerebral cortex and syncope.

Studies have shown that an increase in hydrostatic pressure and, hence, increased vascular wall tension, causes an increase in pulse wave velocity. This would explain the findings, where the PAT to the toes was shorter most likely due to the increase in wall tension and, hence, PWV, and the PAT to the ears and fingers was longer due to a decrease in wall tension and PWV when changing from a supine to standing position. However, overall, the PAT changes from lying supine to standing were not drastic, perhaps due to fast adaptation in vascular tone, autonomic nervous system signals, and myogenic responses.

The initial hypothesis was that the pulse wave arrival should be relatively simultaneous to different peripheral tissue beds despite different distances from the heart. It was believed that a grossly unequal time of pulse arrival would lead to a "steal phenomenon" whereby, in some tissue beds, the pulse wave would have already arrived and have systolic blood pressure, while at other tissues beds where the pulse wave had yet to arrive, the pressure would be diastolic, creating a pressure difference within the valve-less arterial system. By altering the vascular tone, it was believed that the body would maintain a relatively simultaneous pulse wave arrival irrespective of postural change or exercise. However, the pulse arrival to the ear, finger, and toe is not the same and is affected to some degree by position and exercise. The time differences presented by the ratios of PAT were relatively small compared to the distance ratios. For example, the distance from the heart to the ear is on average 5.7 times shorter than to the toe, but the toe/ear PAT ratio ranged from 1.8-2.5 depending on position. This supports the initial hypothesis that the body actively tries to maintain the smallest time difference in pulse wave arrivals to peripheral tissue beds irrespective of its distance from the heart. Interestingly, the ratios are smaller for standing and sitting compared to the supine position, meaning that pulse arrival times are more aligned in the vertical position compared to the horizontal position. A more simultaneous pulse arrival throughout the body is more important in the upright positions when people are likely to be more active.

It is shown in the study that the pulse wave reaches the ear before the index finger or big toe. This may be indicative of the body preferentially diverting blood to the cephalic region, although much more exploratory research is needed before coming to this conclusion. It is also unknown whether this pattern of pulse arrival is still true in individuals not included in the demographic studied (e.g., non-healthy, children, or elderly people), and the data collected in this study could be used as a baseline to which future studies could be compared against. The intended sample population was young and healthy adults.

The PowerLabs converter used was unable to distinguish between pressure generated by capillary filling and extremity movements. Subjects had to stay very still while measurements were being taken to ensure a readable trace. The PowerLabs hardware allowed recordation of only 4 tracings at a time, such that signals from both sides of the body could not be recorded simultaneously. Rather, bilateral measurements were first taken to confirm that each pulse arrived simultaneously to both sides at each level (e.g., toe, finger, and ear).

For the exercise portion, it was difficult to standardize the amount of physical activity based on subjects various fitness and strength levels. Indeed, it would be virtually impossible to find a specific exercise that would be equally intense for every subject. Therefore, squats were chosen as an exercise that would be best suited to each individual's body weight and strength level. In the analysis of data, normalization was not done subjects' blood pressure or heart rate, which have been known to confound PWV assessments.

The choice of the R-wave peak on the EKG as the starting point of the PAT measurements also had its limitations, as it included the pre-ejection systolic phase of ventricular contraction, the period between of isovolumetric ventricular contraction before the opening of the aortic valves. In future studies, the usage of cardiac microphone to record the S1 Korotkoff heart sound could be more appropriate in obtaining a PAT sample.

The pulse wave always arrived at the ear first, then to the index finger, and big toe, respectively, regardless of position or exercise status. This could be simply explained by the difference in distances of the three locations from the heart. PATs were shorter post-exercise irrespective of position, most likely due to an exercise-induced increase in sympathetic activity leading to a global increase in pulse wave velocity. When transitioning from a supine to sitting to standing position, the PAT to the ear and finger decreased, while the PAT to the toe increased. This could be explained by an increase in vascular tone in the lower limbs in response to the increase in hydrostatic pressure during the positional change from horizontal to vertical. The PAT ratios between two locations (i.e., toe/ear and finger/ear) were less than half of their respective length difference ratios. The body strives to maintain a relatively simultaneous pulse arrival at different locations despite a large difference in distance.

In the future, the PAT in the aged and diseased populations can also be studied. It is known that aging and cardiovascular diseases significantly affect the pulse wave velocity, and the presenting mechanisms might be distorted in those groups. The current study could serve as the natural comparison group for future investigations in elderly and patients with CV disease.

Estimation of Stroke Volume and Cardiac Output from Pulse Wave Velocity

The system and method disclosed herein include a real time, continuous, non-invasive technique to estimate SV and CO. Additional details about this system and method are disclosed in "Pilot Study: Estimation of Stroke Volume and Cardial Output from Pulse Wave Velocity" by Yurie Obata, Maki Mizogami, Daniel Nyhan, Dan Berkowitz, Jochen Steppan, and Viachaslau Barodka, which is incorporated herein in its entirety. PWV is a surrogate measure of vascular properties in general, and vascular stiffness in particular. SV and CO estimated from PWV may be comparable to SV and CO derived from TEE. Disclosed herein is a comparison of the accuracy and the trending ability of SV, estimated from PWV, utilizing the Bramwell-Hill equation, with SV measured using TEE in patients undergoing cardiac surgery. PWV-based SV estimation yields reasonable agreement with SV measured by TEE.

The method disclosed herein includes measuring a pulse transit time by superimposing the radial arterial waveform onto the continuous wave Doppler waveform of the left ventricular outflow tract. Using this measurement, the user may calculate SV($SV_{PWV}$) using the transformed Bramwell-Hill equation. The SV measured by TEE($SV_{TEE}$) may be used as a reference.

Stroke volume (SVPWV) was calculated using the transformed Bramwell-Hill equation. The Bramwell-Hill equation allows the estimation of PWV from an increase in the arterial volume (dV), an increase in blood pressure (dP), the arterial tree volume (V), and blood density (ρ).

$$PWV=\sqrt{V/[\rho*dV/dP]} \qquad \text{(Equation 1)}$$

The values dV and dP may be simplified to SV and pulse pressure (PP), respectively, since arterial compliance (dV/dP) is linearly related to SV/PP:

$$PWV=\sqrt{(V/[\rho \times SV/PP])} \qquad \text{(Equation 2)}$$

Solving the equation for SV enables a user to estimate SV from PWV and PP.

$$SV \text{ (ml)}=(133.32 \text{ (N/m}_2) \times V \text{ (ml)} \times PP \text{ (mmHg)})/(\rho \text{ (kg/m}_3) \times PWV^2 \text{ (m}_2\text{/s}_2)) \qquad \text{(Equation 3)}$$

where 1 mmHg is 133.32 N/m$_2$ (N=kg×m/s). Arterial blood volume is estimated as 11% of the total circulating blood volume (TBV). Hence, V was calculated using the formula:

$$V=TBV \times 0.11 \qquad \text{(Equation 4)}$$

TBV was calculated using Nadler's formula with height, weight, and gender as described previously. Ideal body weights (IBW) were used: (Males: IBW=50 kg+2.3 kg for each inch over 5 feet, Females: IBW=45.5 kg+2.3 kg for each inch over 5 feet) for this calculation. When the actual body weight was greater than 30% of the calculated IBW, IBW was replaced to adjusted body weight (ABW: ABW=IBW+0.4×(actual body weight±IBW)). PP was measured from the simultaneously recorded arterial blood pressure waveform. Since blood density does not change significantly with different levels of hemoglobin, it is assumed be a constant value of 1055 kg/m$_3$. Aortic to radial PWV may be used and estimated by dividing the predicted vascular path length (e.g., a distance from the aortic valve to the site of the radial artery catheter) by pulse transit time. The vascular path length may be assumed to be a demi-span (e.g., distance from sternal notch to the tip of the fingers). The demi-span was estimated from height, age, and gender as described previously. The pulse transit time (Δt) is defined as the time from the foot of the CW Doppler waveform (e.g., start of ejection) to the origin of the upstroke on the arterial waveform.

SV of the reference method (SVTEE) was calculated using the formula:

$$SV=LVOT\ SA \times LVOT\ VTI \qquad \text{(Equation 5)}$$

where CSA is the cross sectional area of the LVOT, and VTI is the velocity-time integral across the LVOT. LVOT VTI was measured by tracing the CW Doppler waveform across the aortic valve. Calculation of the LVOT CSA was performed by measuring the LVOT diameter from the mid esophageal long axis view, assuming a circular LVOT. In cases where more than one beat per image was captured, Δt and LVOT VTI were averaged across all beats.

Figure 5A:
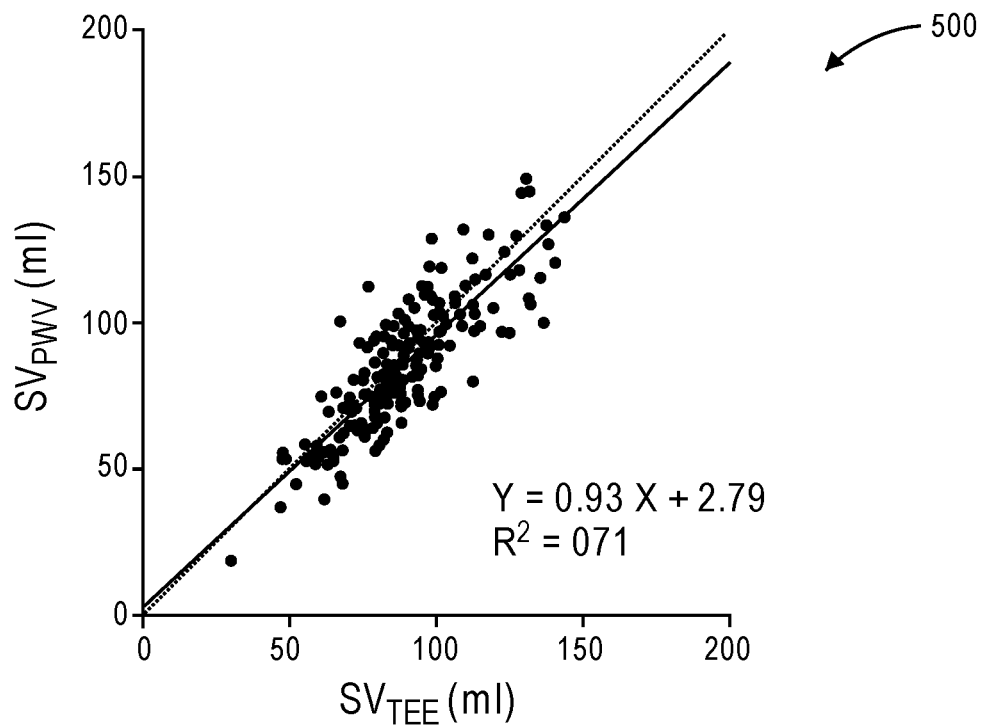
FIG. 5A illustrates a graph showing a correlation between SVPWV and SVTEE.
Figure 5B:
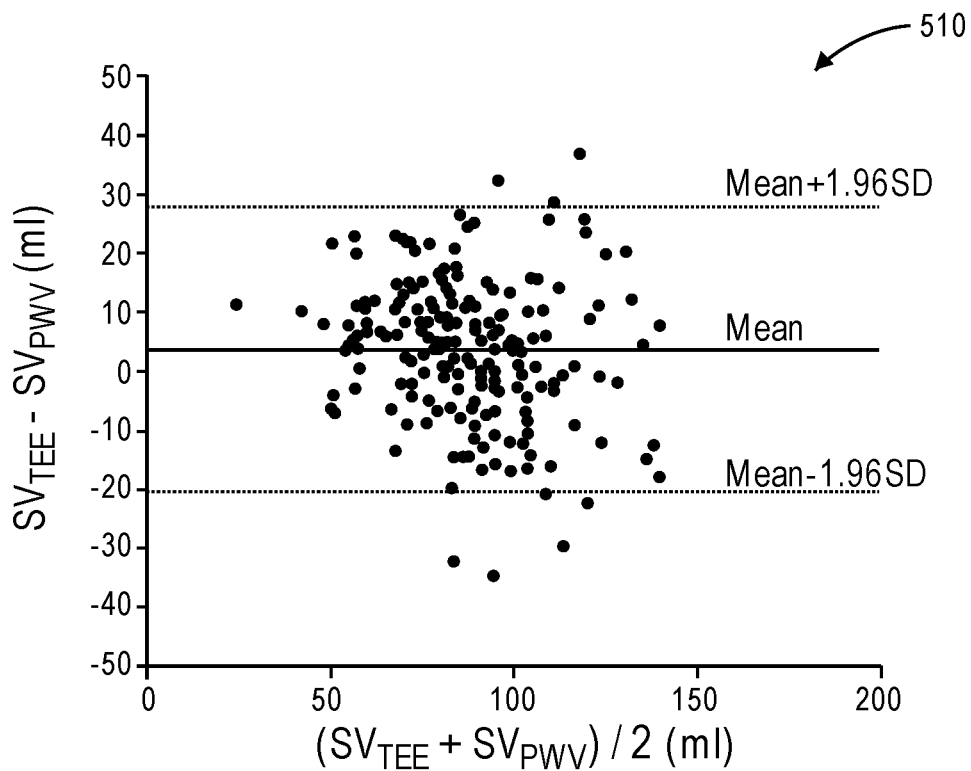
FIG. 5B illustrates a graph showing a bias of 3.70 ml with the limits of agreement ranging from −20.33 to 27.73 ml and a percentage error of 27.4%.

FIG. 5A illustrates a graph 500 showing the correlation between SVPWV and SVTEE. The slope and intercept of the regression were 0.93 (95% confidence interval (CI): 0.84 to 1.01, p<0.0001) and 2.79 (95% CI: −4.96 to 10.54), respectively. The coefficient of determination (R2) was 0.71. Bland-Altman analysis revealed that the bias was 3.70 ml with the limits of agreement ranging from −20.33 to 27.73 ml and a percentage error of 27.4% as presented in the graph 510 in FIG. 5B.

Figure 6:
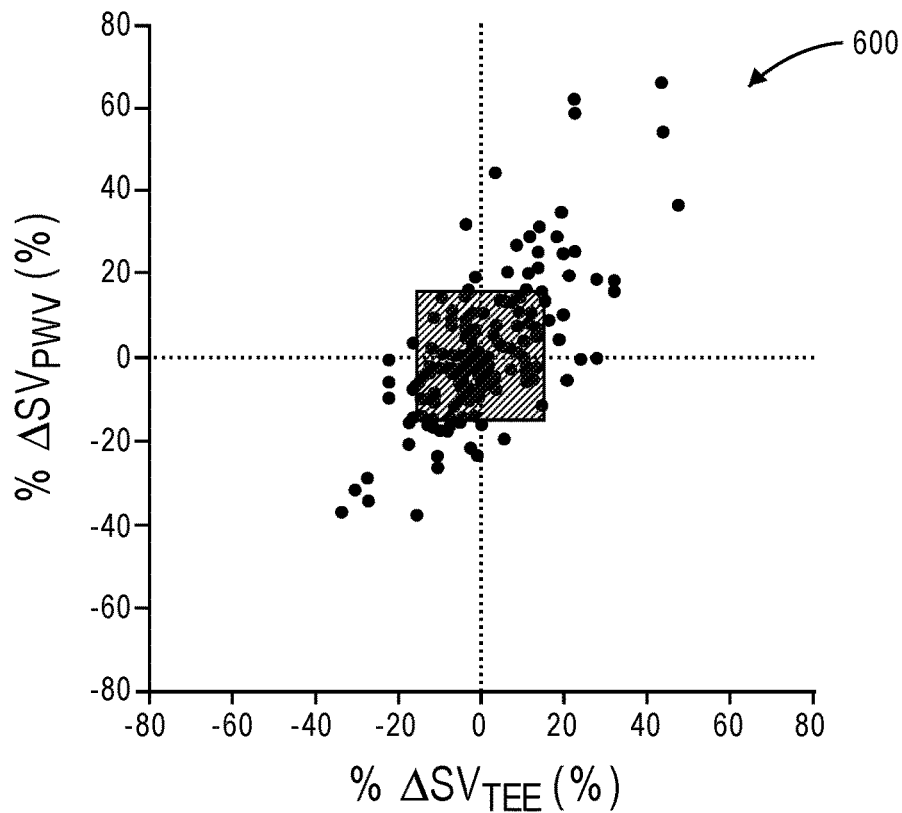
FIG. 6 illustrates a graph showing a four-quadrant plot for % ΔSV data.
Figure 7:
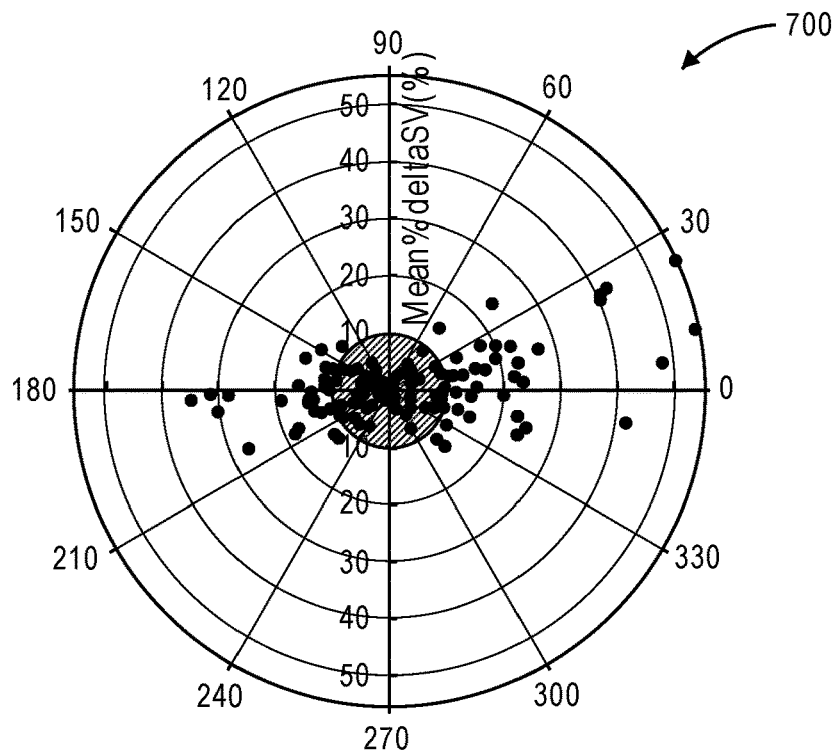
FIG. 7 illustrates a graph showing a polar plot for the % ΔSV data.

FIG. 6 illustrates a graph 600 showing the four-quadrant plot for % ΔSV data. Out of 162 depicted pairs, 102 pairs were located within the 15% exclusion zone (shaded area). Out of 60 pairs included in the calculation of concordance rate, 51 pairs were located in either the upper right or lower left quadrant, hence, the calculated concordance rate from the four-quadrant plot was 85.0% (51/60×100%). The polar plot for the % ΔSV data is shown in the graph 700 of FIG. 7. Out of 162 depicted pairs, 98 pairs were located within the 10% exclusion zone (shaded area). The mean (SD) angular bias was 1.38 (20.73) degrees with the radial limits of agreement of ±41.5 degrees. Out of 64 pairs included in the calculation of angular concordance rate, 55 pairs were located within ±30 degrees. Hence, the calculated concordance rate for the polar data points was 85.9% (55/64×100%).

SV, as estimated from PWV, is in good agreement with SV measured by TEE in patients undergoing cardiac surgery. The PWV-based SV calculation produced a very small and clinically insignificant bias (3.70 ml) with a percentage error of 27.4%, indicating that the agreements of absolute values between SVPWV and SVTEE are clinically acceptable.

The reliable real-time tracking of changes in CO may be more important than the ability to deliver a highly accurate single measurement. In the tests of trending ability, PWV-based SV estimation showed promising results reaching a concordance rate of 85.0% in the four-quadrant plot analysis and radial limits of agreement of ±41.5 degrees in the polar plot analysis when compared to a TEE based SV estimation.

Clinically, a user can obtain pulse transit time and PWV by using non-invasive or minimally-invasive techniques. Pulse transit time can be estimated from the peak of the R wave on EKG or from the beginning of the S1 sound of phonocardiogram to the initiation of the upstroke on the radial arterial tonometry waveform (or the plethysmograph waveform). Thus, the potential benefit of the method as a clinical monitor of CO is its ability to estimate SV and CO in a non-invasive, continuous way. Moreover, this technique has a strong potential to be automated by real-time computerized signal analysis of the EKG, phonocardiogram, and pulse plethysmogram waveforms, which would make it non-invasive and continuous.

SV may be estimated from PWV using the Bramwell-Hill equation. The method does not need calibration, but it may use knowledge of the patients' heights, weights, genders, and/or measurements of pulse wave velocity and pulse pressure. SV estimated from PWV was clinically acceptable and interchangeable with SV measured by TEE. Although the trending ability didn't reach the defined acceptable range, the PWV based SV/CO monitor shows clinical promise since it is real-time, non-invasive, and continuous. Further, studies in patient population with rapid changes in volume status such as hemorrhage are required to investigate the clinical utility of the proposed methodology.

Difference Between Ejection Times Measured at Two Different Peripheral Locations as a Marker of Vascular Stiffness PWV may be used as an arterial damage assessment tool and a surrogate of arterial stiffness. However, the current technology does not allow a user to measure PWV both continuously and in real-time. Peripherally measured ET overestimates the ET measured centrally. This difference in ET is associated with the inherent vascular properties. ETs derived from plethysmography simultaneously at different peripheral locations may be examined. Moreover, the influence of the underlying arterial properties on ET prolongation by changing the subject's position may be examined. The ET difference between two peripheral locations (ΔET) and its corresponding PWV for the same heartbeat may be calculated. The ΔET increased with a corresponding decrease in PWV. The difference between ΔET in the supine and standing (ΔΔET) was higher in young subjects with low mean arterial pressure (MAP) and low PWV. These results suggest that the ET difference represents the underlying vascular properties. ΔET may be a real-time continuous and non-invasive parameter of vascular properties, and the ΔΔET as a potential non-invasive parameter of vascular reactivity.

The user may distinguish patients with a compliant vasculature from those with stiff vessels. One standard to measure vascular stiffness is carotid-femoral PWV (cf-PWV), which has been recommended by the European Society of Hypertension and the European Society of Cardiology (ESH/ESC) as a marker for arterial damage and by the American Heart Association (AHA)'s Scientific Statement as a surrogate for arterial stiffness. However PWV depends not only on intrinsic vascular stiffness but also on vessel wall tension, which dynamically changes with fluctuations in blood pressure (BP). Several attempts have been made to develop a BP-independent index of vascular stiffness, such as Cardio-Ankle Vascular Index (CAVI) and the Arterial Stiffness Index (ASI). However, they are not consistently BP-independent in all clinical scenarios. Moreover, the current technology for PWV measurement does not allow the user to determine this index continuously and in real-time. Hence, there is a clinical need to develop a real-time, continuous, and non-invasive marker of vascular stiffness. Additional details about a real-time, continuous, and non-invasive marker of vascular stiffness are disclosed in "Difference Between Ejection Times Measured at Two Different Peripheral Locations as Novel Marker of Vascular Stiffness" by Yurie Obata, Pavel Ruzankin, Dan Berkowitz, Jochen Steppan, and Viachaslau Barodka, which is incorporated herein in its entirety.

The arterial blood pressure waveform changes as the pulse wave travels across the arterial tree to different peripheral locations. The peripherally measured ejection time, derived from the radial artery blood pressure waveform, consistently overestimates a centrally measured ejection time at lower BPs, slow HRs, and low PWVs. This prolongation is most likely due to the dynamic interaction between the left ventricle (LV) and the vasculature and represents a direct modulating effect of the vasculature on the pulse waveform.

The ET may be extracted from the difference between the dicrotic notch arrival time (DAT) and the corresponding pulse arrival time (PAT) for each location (e.g., ear, finger, and toe) and position (e.g., standing, sitting, and supine). The DAT at each location may be obtained by calculating the time delay between the peak of the R wave on the EKG and the start of the dicrotic notch on the plethysmograph waveform. The PAT at each location may be obtained by calculating the time delay between the peak of the R wave on the EKG waveform and the initiation of the upstroke on the plethysmograph waveform.

The time difference between the ET at the toe and the ET at the ear ($\Delta ET_{Toe-Ear}$), between the ET at the toe and the ET at the finger ($\Delta ET_{Toe-Finger}$), and between the ET at the finger and the ET at the ear ($\Delta ET_{Finger-Ear}$) was calculated in each position for each subject and the same heartbeat. ΔPAT and ΔDAT were calculated in the same way ($\Delta PAT_{Toe-Ear}$, $\Delta PAT_{Toe-Finger}$, $\Delta PAT_{Finger-Ear}$, $\Delta DAT_{Toe-Ear}$, $\Delta DAT_{Toe-Finger}$, and $\Delta DAT_{Finger-Ear}$).

"ΔΔET" is defined as the difference between the mean of ΔET in the standing and supine positions in each individual subject for each pair of locations by subtracting the former from the latter. "ΔPWV" is defined as the difference between the mean of PWV in the standing and supine positions in each individual subject for each pair of locations by subtracting the latter from the former. ΔΔET may be calculated as an index reflecting the effect of both measurement sites and positions on ET prolongation.

Figure 8:
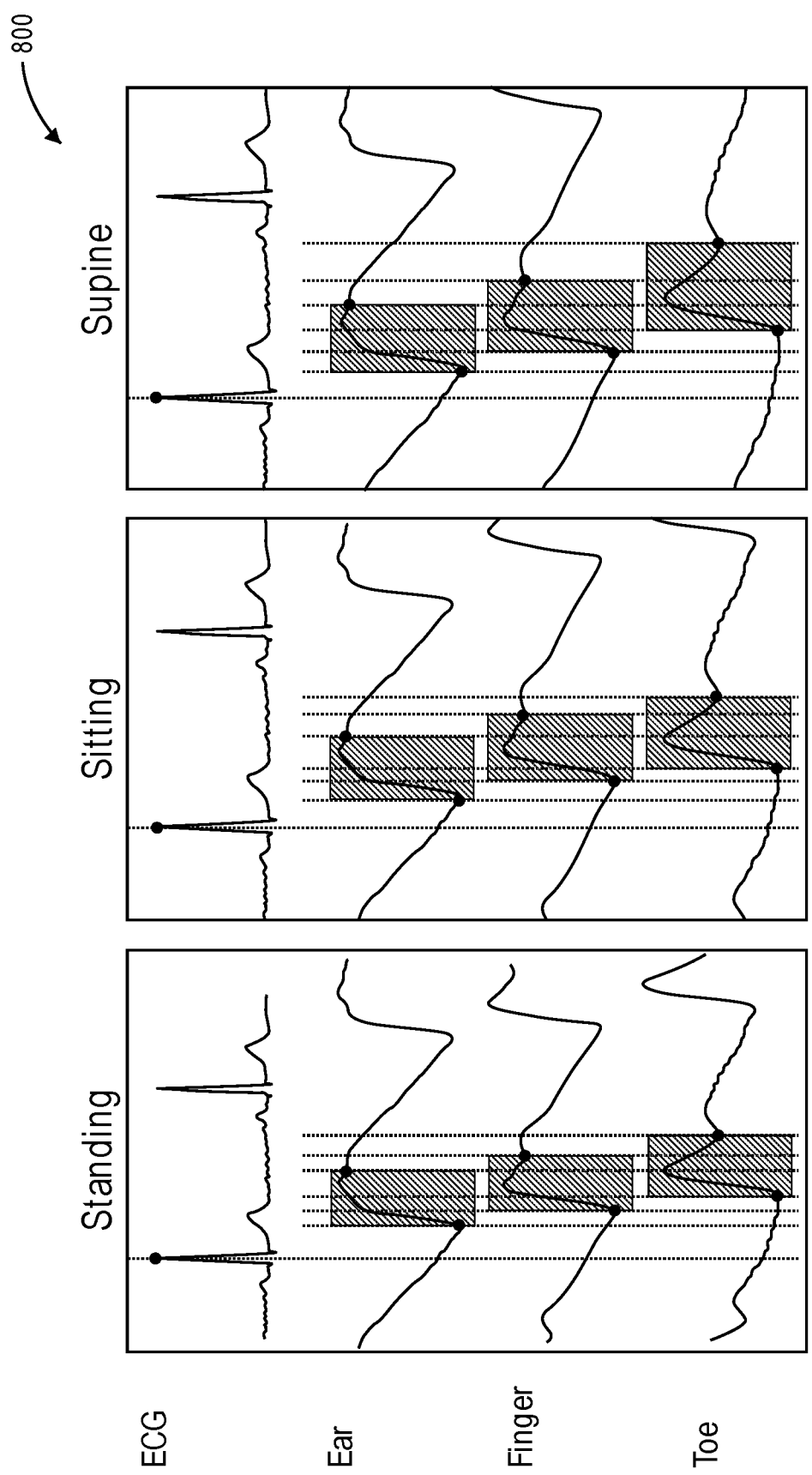
FIG. 8 illustrates graphs showing a schematic representation of the simultaneously recorded electrocardiogram and plethysmograph waveforms at the ear, finger, and toe in the standing, sitting and supine positions.

FIGS. 8A-8C illustrate graphs 800, 810, 820 of the simultaneously recorded electrocardiogram and plethysmograph waveforms at the ear, finger, and toe in the standing, sitting and supine positions. The dots on the EKG waveforms indicate the peak of the R wave, and the dots on the plethysmograph waveforms indicate the beginning of the upstroke of the pulse waveform and the dicrotic notch. The ETs are shaded in gray between the start of the upstroke and the dicrotic notch on the plethysmograph waveform. The waveform presented was obtained from a single subject from each location, but the duration of the ET and the dots represent average times, as calculated from all subjects.

FIGS. 9A-9I illustrate graphs 900, 910, 920, 930, 940, 950, 960, 970, 980 showing the relationship between ΔET and ΔPAT (FIGS. 9A, 9D, 9G), between ΔET and ΔDAT (9B, 9E, 9H), between ΔDAT and ΔPAT (FIGS. 9C, 9F, 9I) for each pair of locations (Toe-Ear: 9A, 9B, 9C, Toe-Finger: 9D, 9E, 9F, Finger-Ear: 9G, 9H, 9I). Each individual subject has three dots on the each graph which indicate mean values derived from the standing (circles), sitting (triangles) and supine (squares) positions. The dashed lines indicate the linear regression. The regression equation, the coefficient of determination ($R^2$), and P value are presented. The ΔET between all pairs of locations correlated with the corresponding ΔPAT and ΔDAT. The $R^2$ was higher for ΔDAT compared to ΔPAT for all pairs of locations. The best correlation was observed for the difference in ETs between the toe and ear ($\Delta ET_{Toe-Ear}$) compared to the difference in DAT ($\Delta DAT_{Toe-Ear}$) with $R^2=0.86$.

Figure 9A:
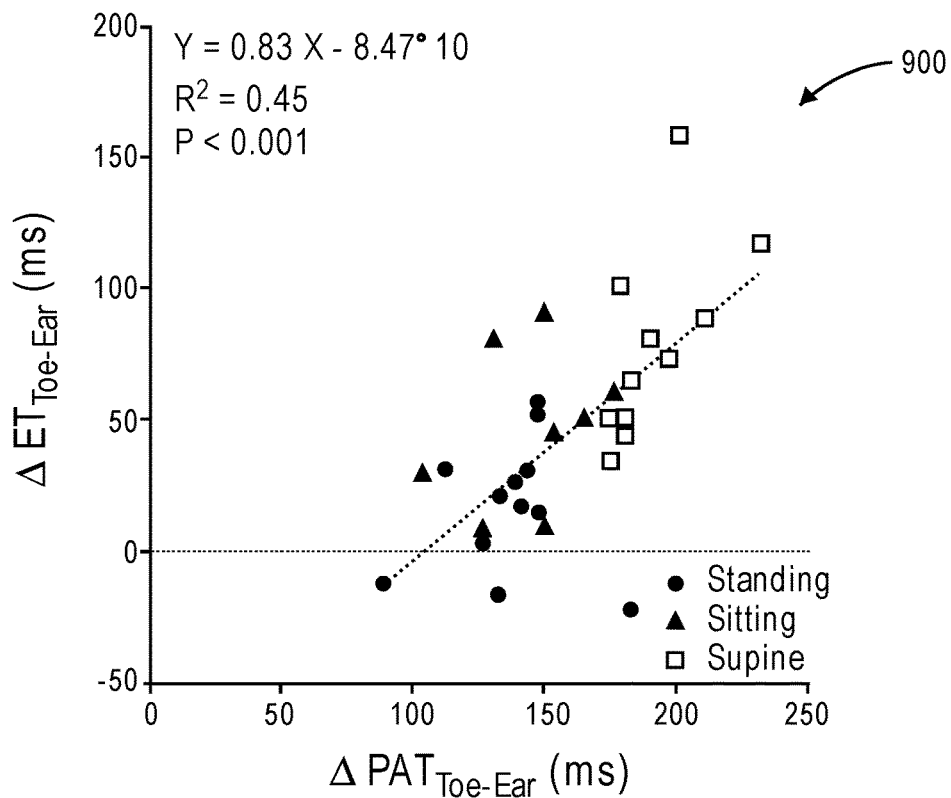
FIGS. 9A-9I illustrate graphs showing the relationship between ΔET and ΔPAT (FIGS. 9A, 9D, 9G), between ΔET and ΔDAT (9B, 9E, 9H), between ΔDAT and ΔPAT (FIGS. 9C, 9F, 9I) for each pair of locations (Toe-Ear.
Figure 9B:
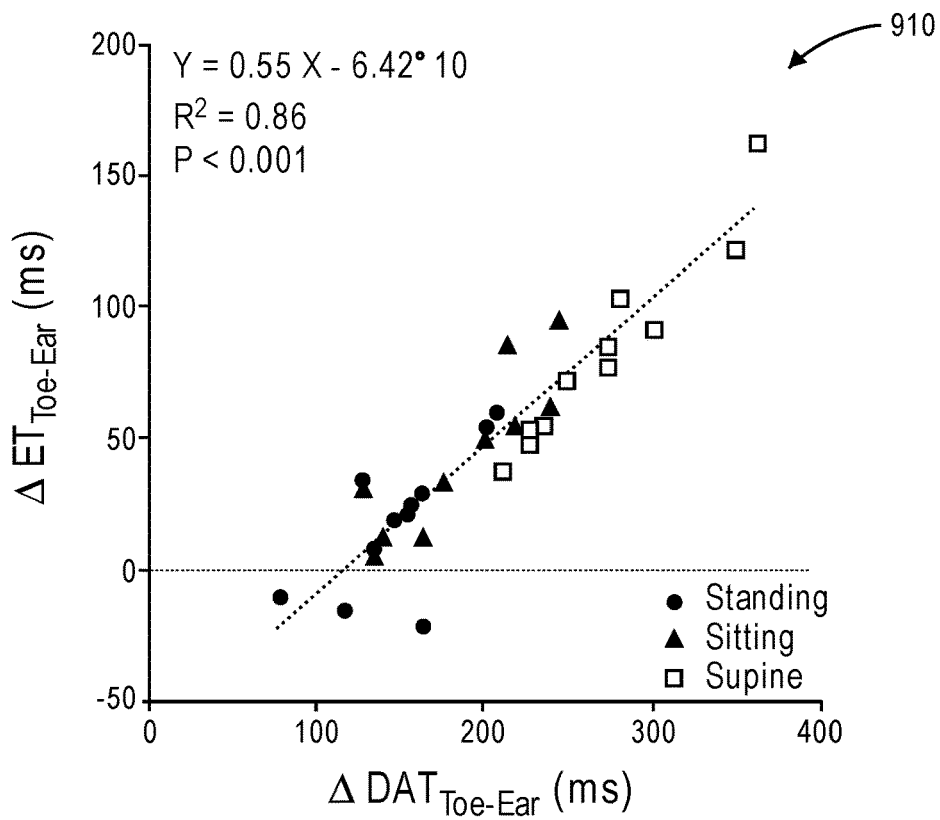
Figure 9C:
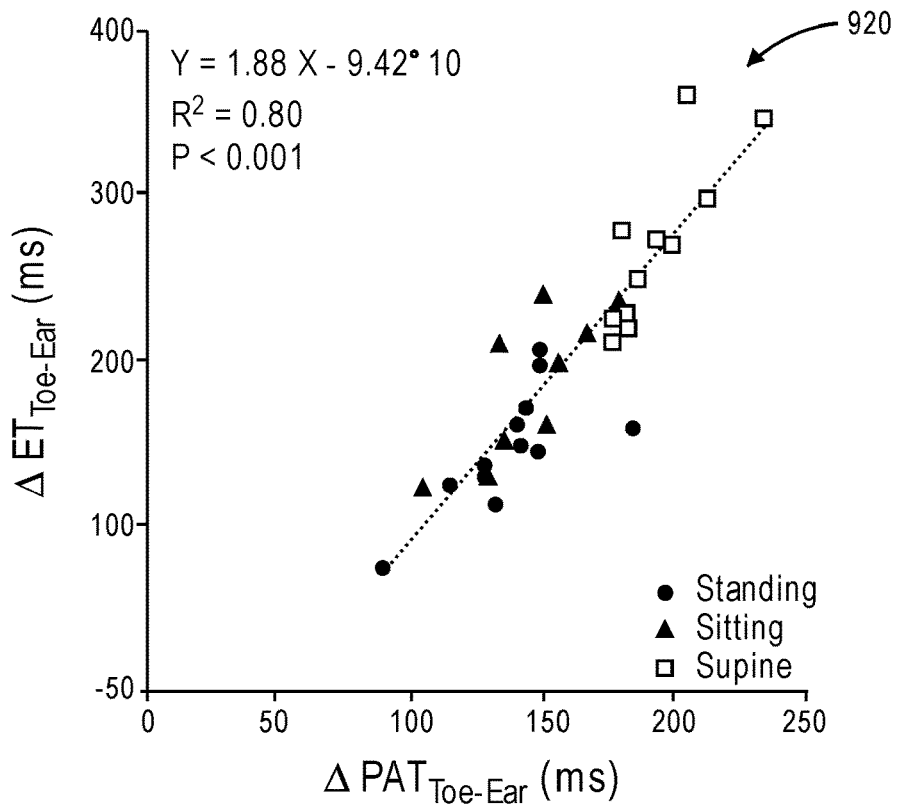
Figure 9D:
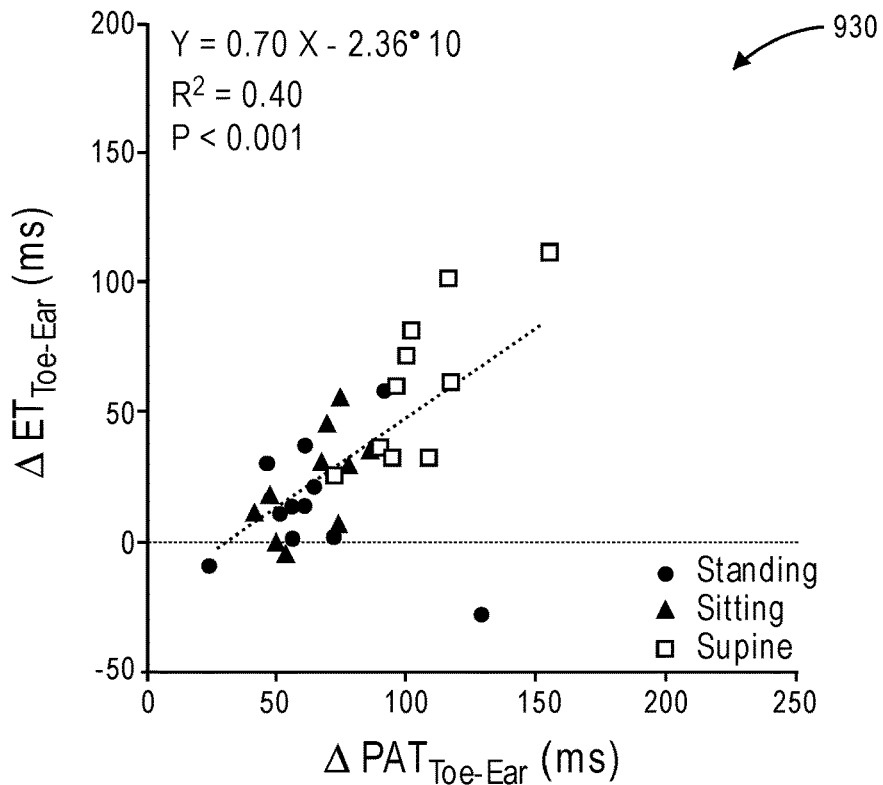
Figure 9E:
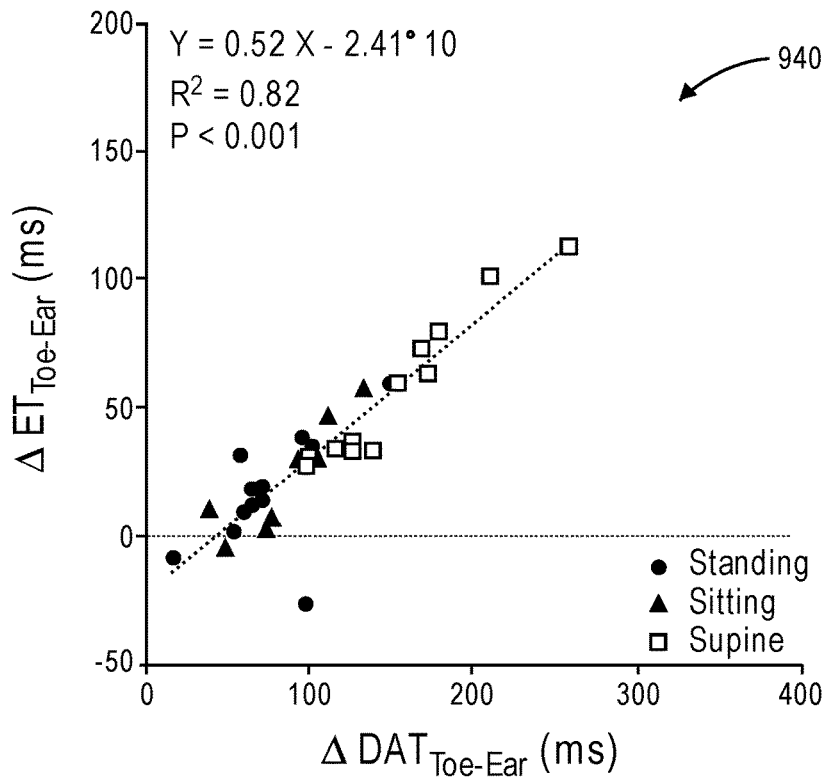
Figure 9F:
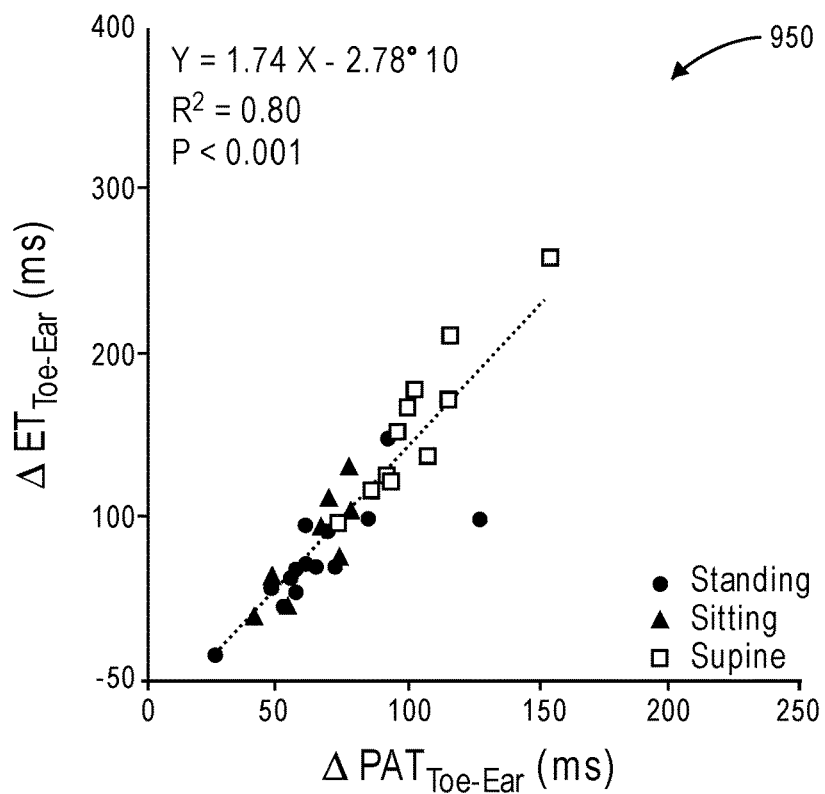
Figure 9G:
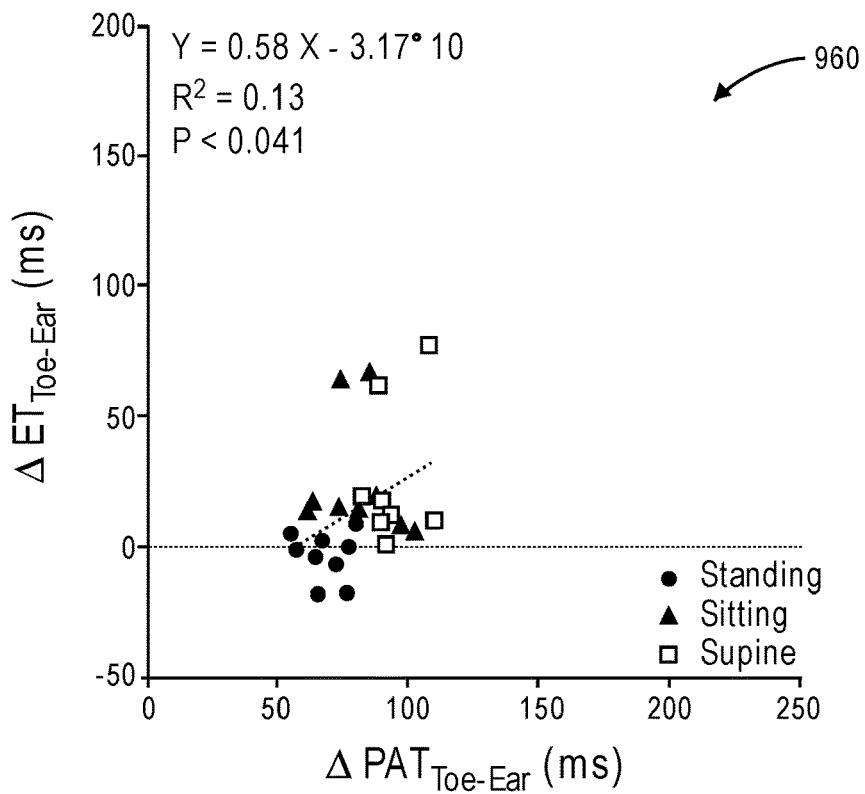
Figure 9H:
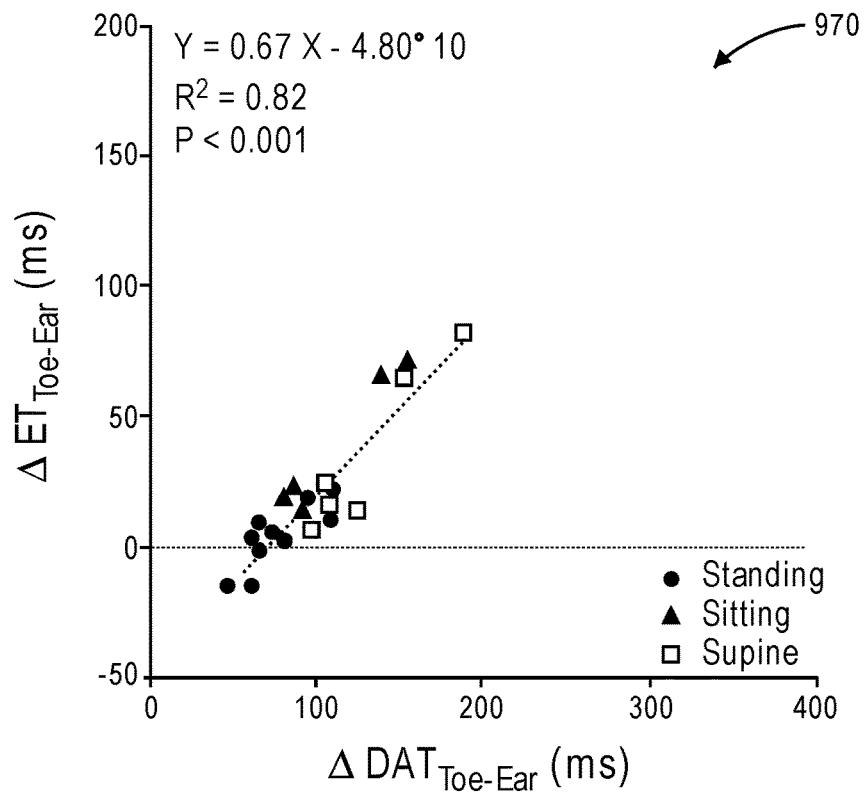
Figure 9I:
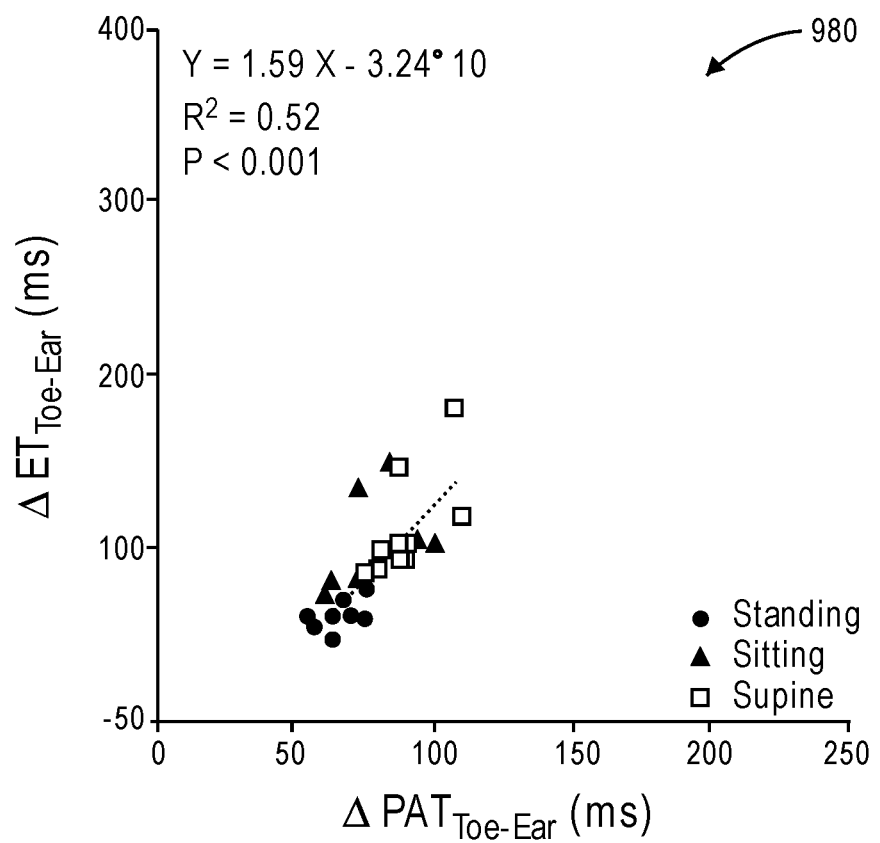

ΔET decreased exponentially with increasing PWV (either based on ΔPAT or ΔDAT) for each pair of locations (FIGS. 9A, 9B, 9D, 9E, 9G and 9H). $R^2$ was higher for $PWV_{\Delta DAT}$ compared to $PWV_{\Delta PAT}$ in all pairs of locations. $PWV_{\Delta DAT}$ correlated well with $PWV_{\Delta PAT}$ with a $R^2=0.89$ for toe-finger (FIG. 9F).

Figure 10A:
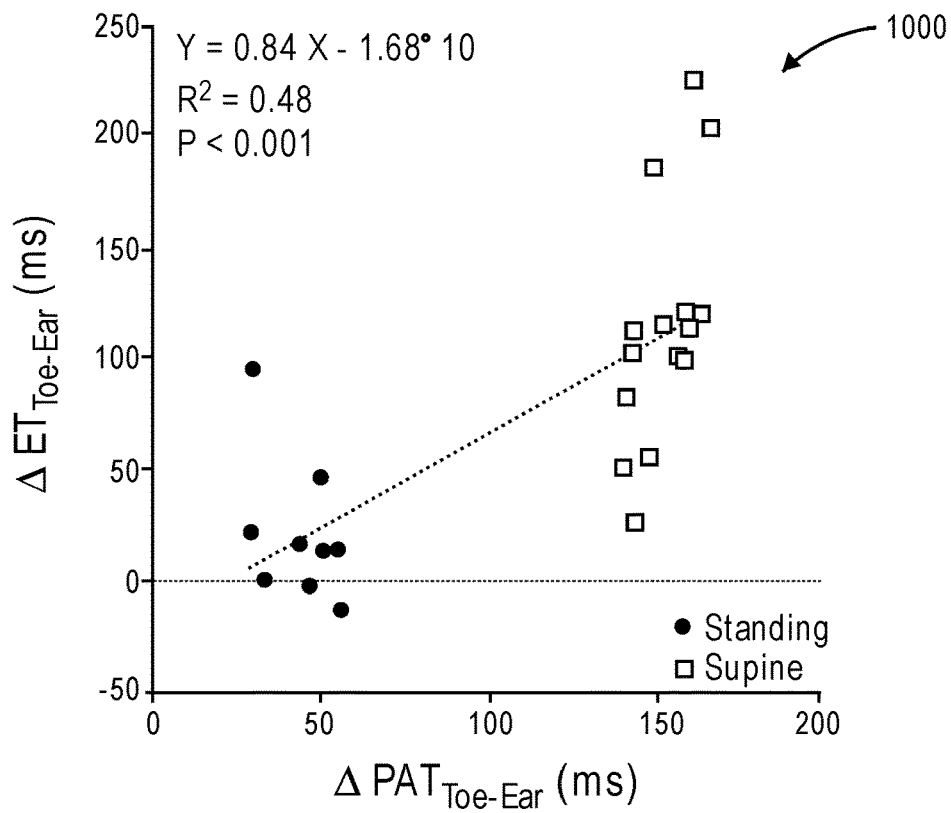
FIGS. 10A, 10B, and 10C illustrate graphs showing the relationships between $\Delta ET_{Toe-Finger}$, $\Delta PAT_{Toe-Finger}$, and $\Delta DAT_{Toe-Finger}$, respectively, as derived from a subject with a more compliant vasculature.
Figure 10B:
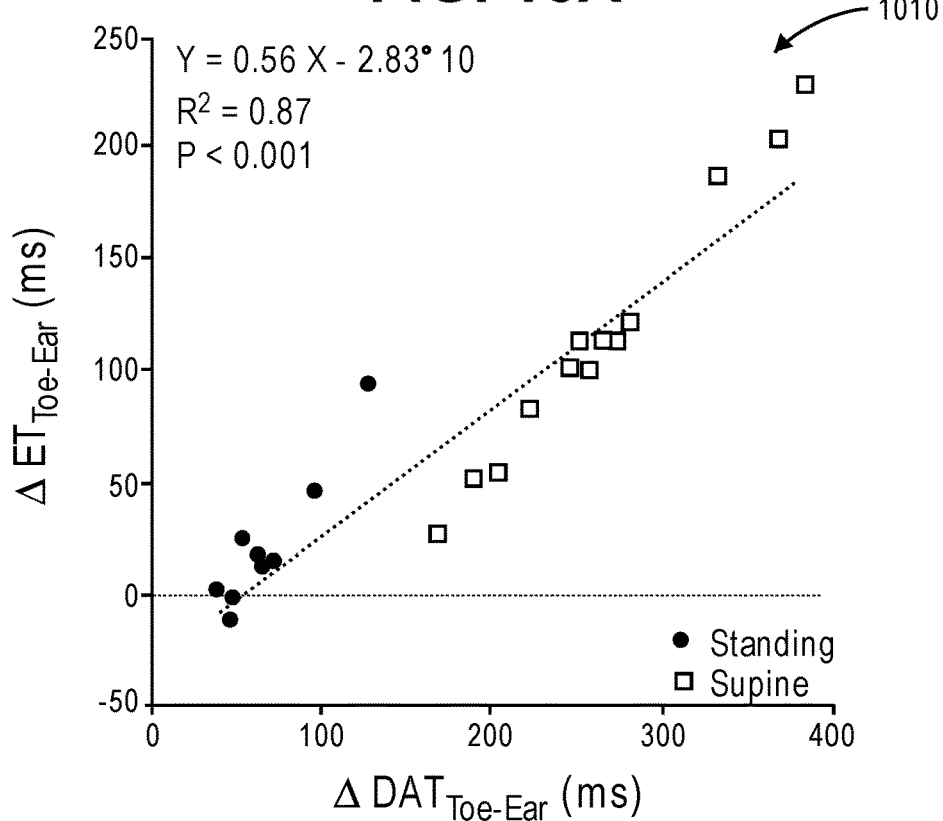
Figure 10C:
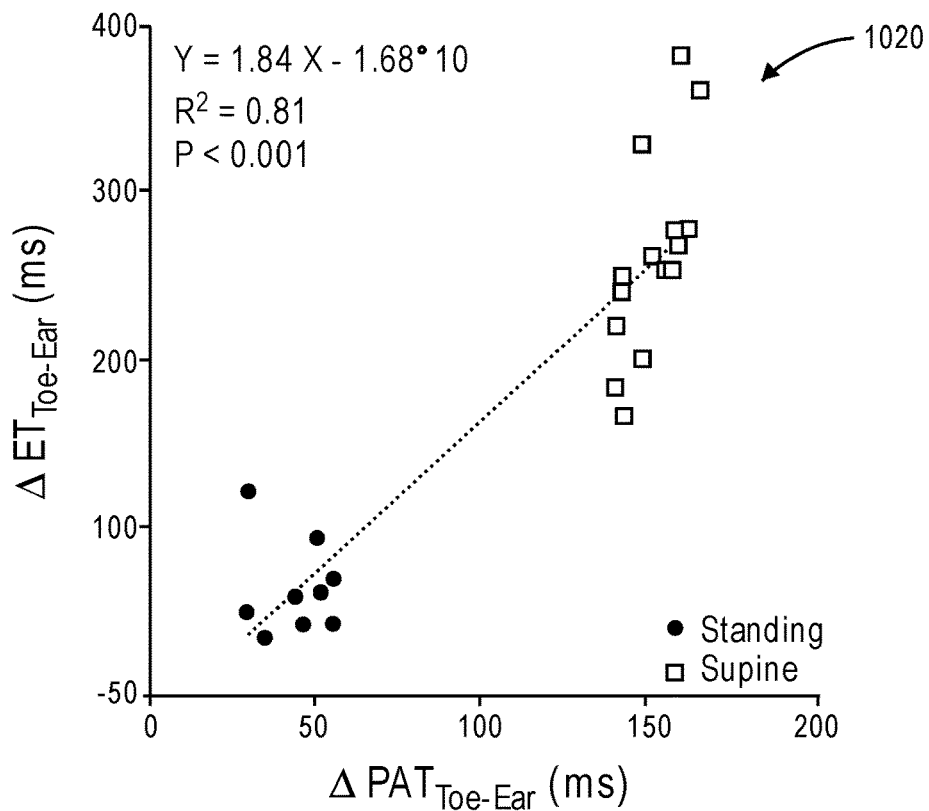

FIGS. 10A-10F depict graphs 1000, 1010, 1020, 1030, 1040, 1050 showing the relationships between $\Delta ET_{Toe\text{-}Finger}$, $\Delta PAT_{Toe\text{-}Finger}$, and $\Delta DAT_{Toe\text{-}Finger}$ in two subjects. One subject had a more compliant vasculature, and the other a less compliant vasculature, based on $PWV_{\Delta PAT\ Toe\text{-}Finger}$ in the supine position. FIGS. 10A, 10B and 10C show the relationships between $\Delta ET_{Toe\text{-}Finger}$, $\Delta PAT_{Toe\text{-}Finger}$, and $\Delta DAT_{Toe\text{-}Finger}$ as derived from the subject with the more compliant vasculature ($PWV_{\Delta PAT\ Toe\text{-}Finger}$ of 3.90 m/s in the supine position and 12.79 m/s in the standing position in a 23 year old female). $\Delta ET_{Toe\text{-}Finger}$, $\Delta PAT_{Toe\text{-}Finger}$, and $\Delta DAT_{Toe\text{-}Finger}$ varied with changing positions, with $\Delta ET_{Toe\text{-}Finger}$ and $\Delta DAT_{Toe\text{-}Finger}$ varying more than $\Delta PAT_{Toe\text{-}Finger}$. The average of $\Delta ET_{Toe\text{-}Finger}$ was 28.3 ms while standing and increased 3.8 times in the supine position to 108.2 ms in this young female with a compliant vasculature. The difference in absolute values between $\Delta ET_{Toe\text{-}Finger}$ supine and standing ($\Delta\Delta ET_{Toe\text{-}Finger}$) was 79.9 ms.

Figure 10D:
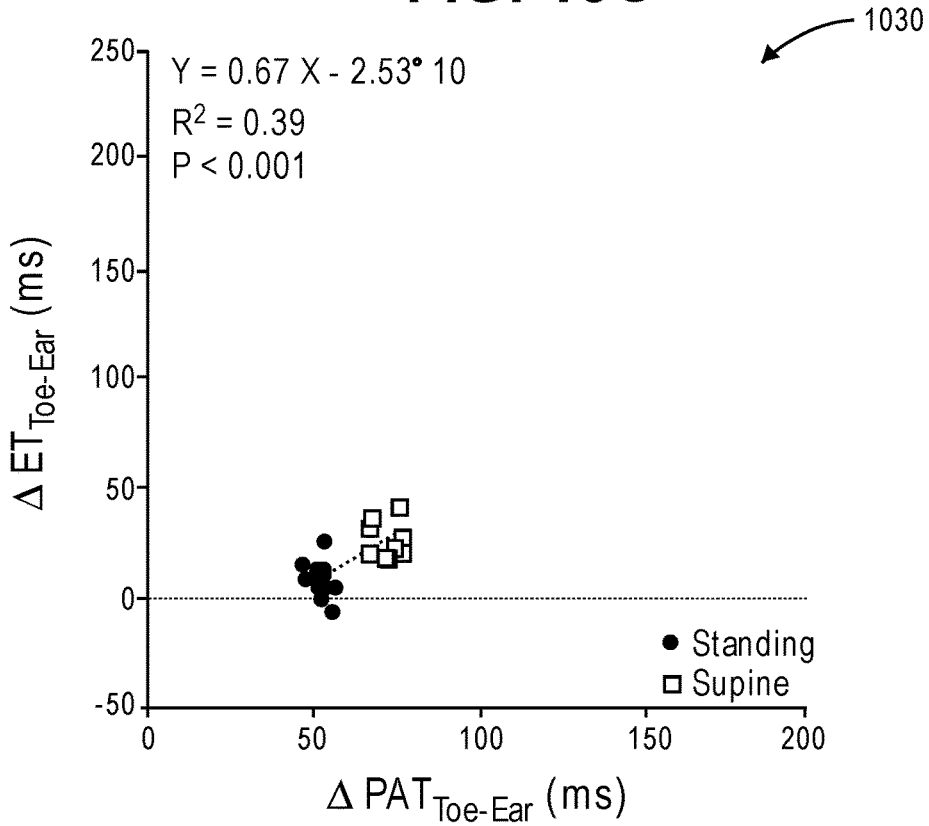
FIGS. 10D, 10E and 10F illustrate graphs showing the relationship between $\Delta ET_{Toe-Finger}$, $\Delta PAT_{Toe-Finger}$, and $\Delta DAT_{Toe-Finger}$, respectively, as derived from a subject with a less compliant vasculature.
Figure 10E:
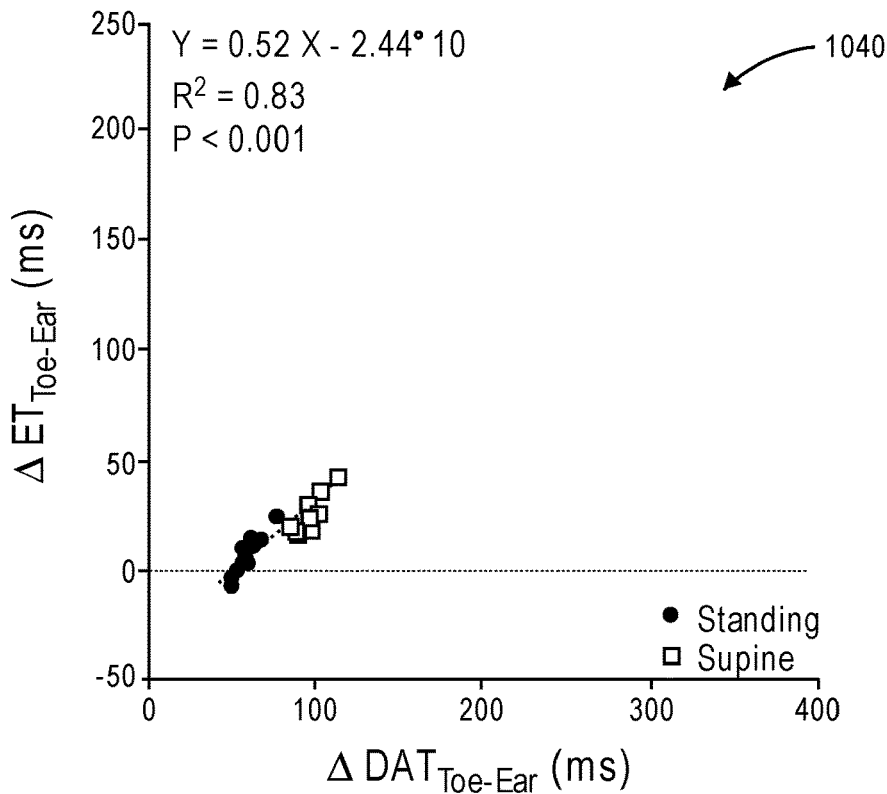
Figure 10F:
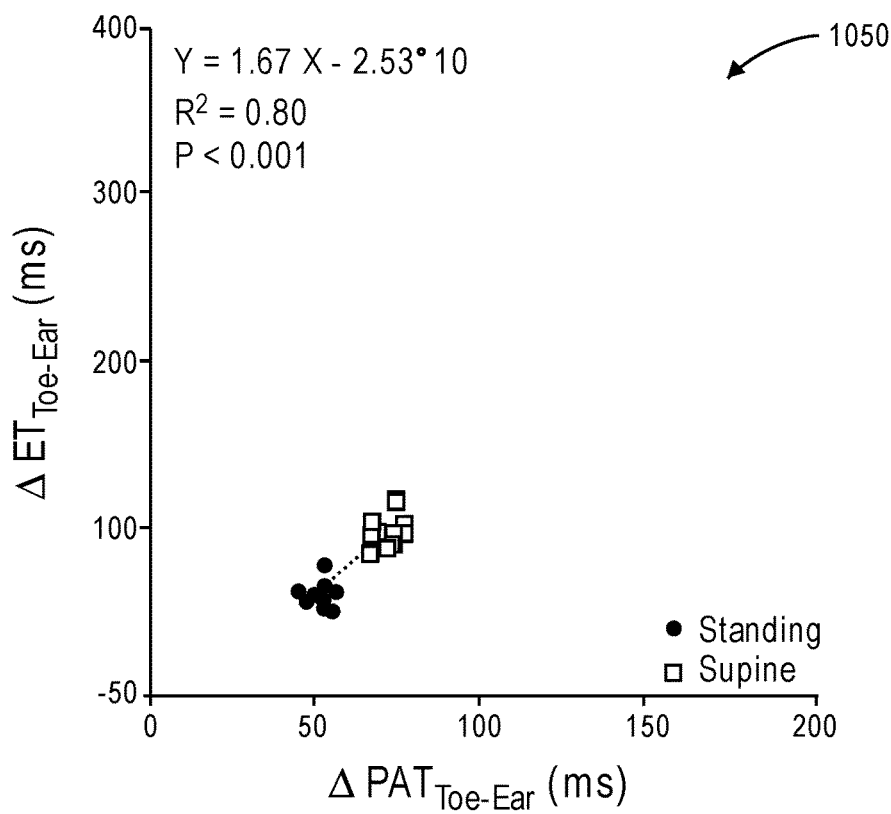

FIGS. 10D, 10E and 10F show the relationship between $\Delta ET_{Toe\text{-}Finger}$, $\Delta PAT_{Toe\text{-}Finger}$, and $\Delta DAT_{Toe\text{-}Finger}$ derived from the subject with the less compliant vasculature as evident by highest $PWV_{\Delta PAT}$ Toe-Finger in the supine position ($PWV_{\Delta PAT\ Toe\text{-}Finger}$ of 8.06 m/s in the supine position and 11.08 m/s in the standing position in a 36 years old female). The variation of $\Delta ET_{Toe\text{-}Finger}$, $\Delta PAT_{Toe\text{-}Finger}$, and $\Delta DAT_{Toe\text{-}Finger}$ were small compared to the subject with the more compliant vasculature. The average $\Delta ET_{Toe\text{-}Finger}$ was 8.7 ms when standing and increased 2.8 times in the supine position to 24.2 ms. The difference in absolute values between $\Delta ET_{Toe\text{-}Finger}$ supine and standing ($\Delta\Delta ET_{Toe\text{-}Finger}$) was 15.5 ms, which is 5.2 times less than the 79.9 ms observed in the subject with the more compliant vasculature.

Given that there was a significant change in $\Delta\Delta ET_{Toe\text{-}Finger}$ between the two subjects with the more and less compliant vasculatures, this parameter, $\Delta\Delta ET_{Toe\text{-}Finger}$, may be explored in all subjects.

$\Delta\Delta ET_{Toe\text{-}Finger}$ correlated moderately and significantly with age, MAP, and $PWV_{\Delta PAT\ Toe\text{-}Finger}$ such that increased age, MAP, and $PWV_{\Delta PAT\ Toe\text{-}Finger}$ were associated with decreased $\Delta\Delta ET_{Toe\text{-}Finger}$ (age vs $\Delta\Delta ET_{Toe\text{-}Finger}$: $R^2=0.55$, P=0.009; MAP vs $\Delta\Delta ET_{Toe\text{-}Finger}$: $R^2=0.64$, P=0.003; $PWV_{\Delta PAT\ Toe\text{-}Finger}$ VS $\Delta\Delta ET_{Toe\text{-}Finger}$: $R^2=0.39$, P=0.041). However, $\Delta\Delta ET_{Toe\text{-}Finger}$ did not correlate with BMI, HR, or $\Delta PWV_{\Delta PAT\ Toe\text{-}Finger}$ (BMI vs $\Delta\Delta ET_{Toe\text{-}Finger}$: $R^2=0.14$, P=0.25; HR vs $\Delta\Delta ET_{Toe\text{-}Finger}$: $R^2=0.01$, P=0.77; $\Delta PWV_{\Delta PAT\ Toe\text{-}Finger}$ VS $\Delta\Delta ET_{Toe\text{-}Finger}$: $R^2=0.02$, P=0.67).

Figure 11A:
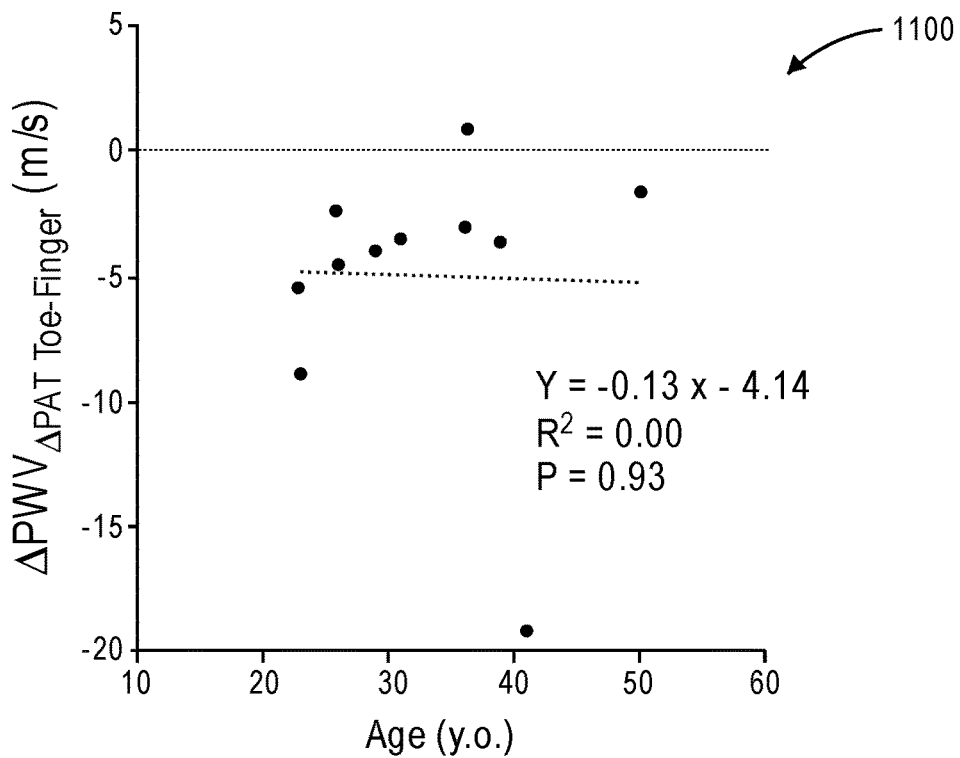
FIGS. 11A-E illustrate graphs showing: $\Delta PWV_{\Delta PAT\ Toe-Finger}$ as a function of age (FIG. 11A), $\Delta PWV_{\Delta PAT\ Toe-Finger}$ as a function of BMI (FIG. 11B), $\Delta PWV_{\Delta PAT\ Toe-Finger}$ as a function of HR measured in the supine position (FIG. 11C), $\Delta PWV_{\Delta PAT\ Toe-Finger}$ as a function of MAP measured in the supine position (FIG. 11D), and $\Delta PWV_{\Delta PAT\ Toe-Finger}$ as a function of $PWV_{\Delta PAT\ Toe-Finger}$ in the supine position (FIG. 11E).
Figure 11B:
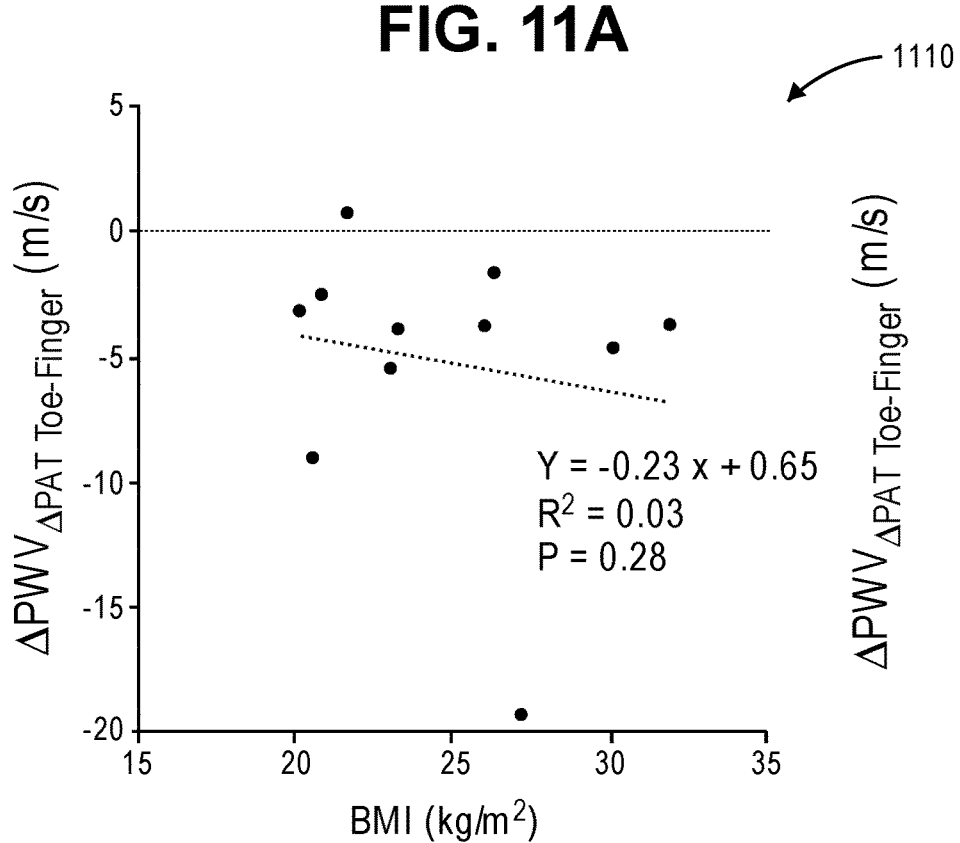
Figure 11C:
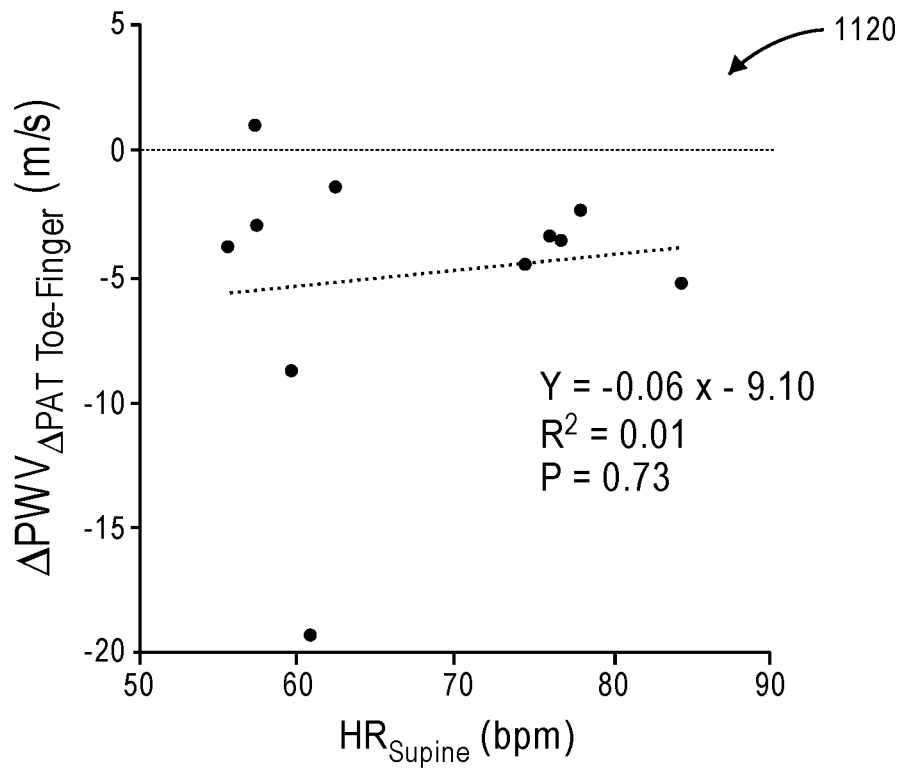
Figure 11D:
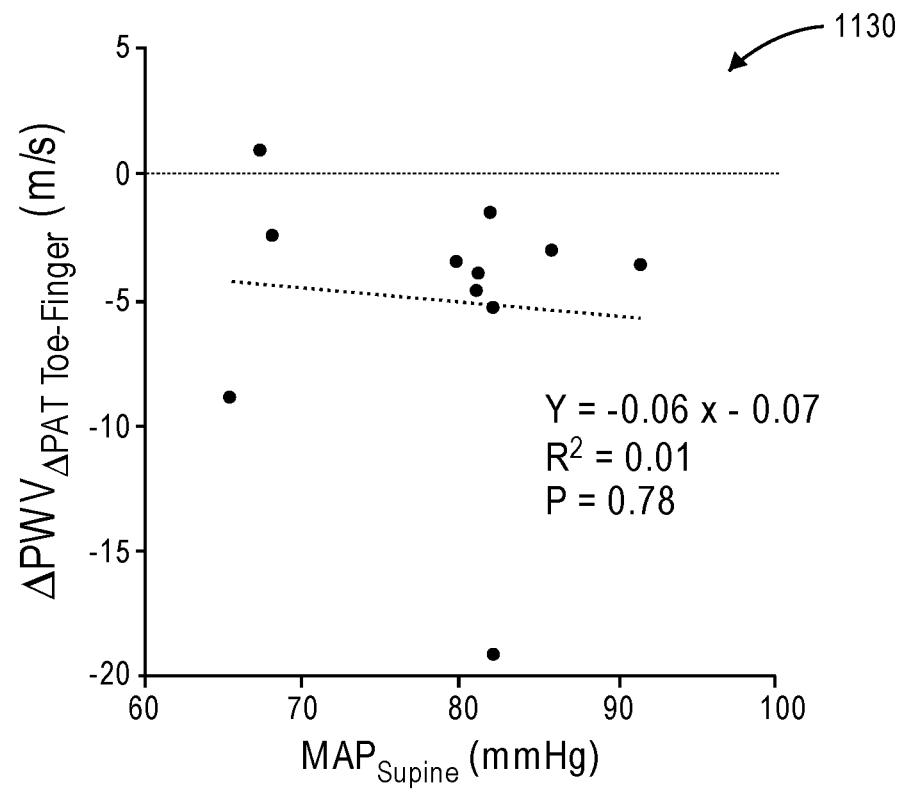
Figure 11E:
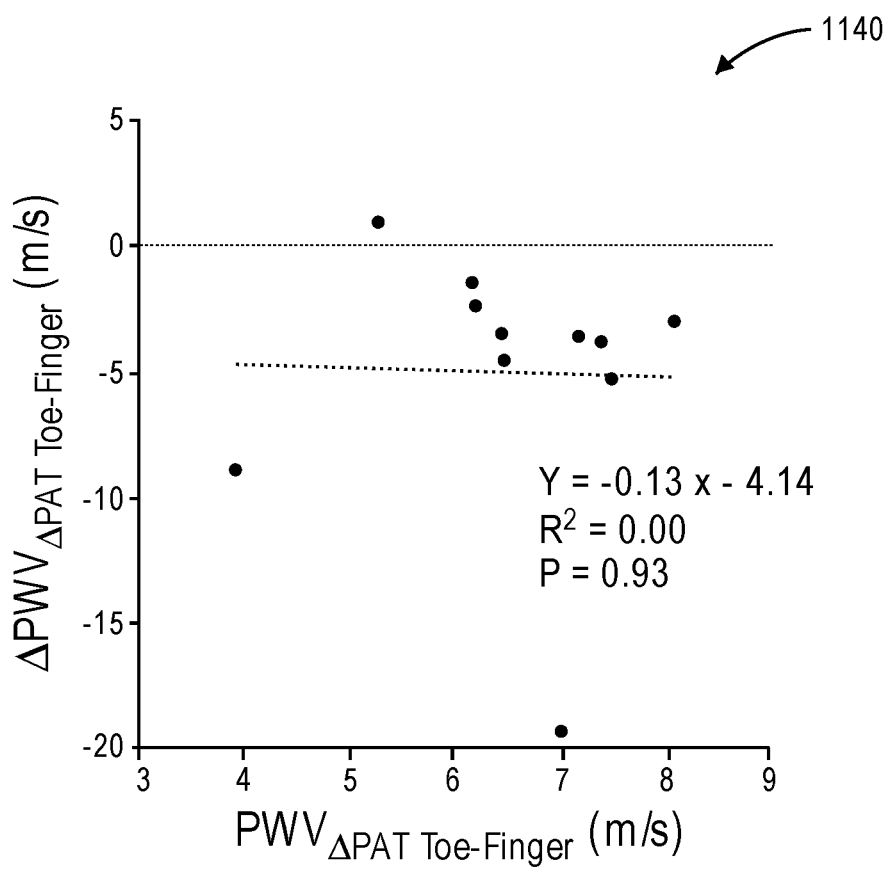

FIGS. 11A-E illustrate graphs 1100, 1110, 1120, 1130, 1140 showing: $\Delta PWV_{\Delta PAT\ Toe\text{-}Finger}$ as a function of age (FIG. 11A), $\Delta PWV_{\Delta PAT\ Toe\text{-}Finger}$ as a function of BMI (FIG. 11B), $\Delta PWV_{\Delta PAT\ Toe\text{-}Finger}$ as a function of HR measured in supine position (FIG. 11C), $\Delta PWV_{\Delta PAT\ Toe\text{-}Finger}$ as a function of MAP measured in supine position (FIG. 11D), and $\Delta PWV_{\Delta PAT\ Toe\text{-}Finger}$ as a function of $PWV_{\Delta PAT\ Toe\text{-}Finger}$ in supine position (FIG. 11E). The effect of age, BMI, HR, MAP, $PWV_{\Delta PAT\ Toe\text{-}Finger}$, and $\Delta PWV_{\Delta PAT\ Toe\text{-}Finger}$ on $\Delta ET_{Toe\text{-}Finger}$ in the supine position may be similar to $\Delta\Delta ET_{Toe\text{-}Finger}$. $R^2$ was lower for age vs $\Delta ET_{Toe\text{-}Finger}$ ($R^2=0.30$, P=0.08), and for MAP vs $\Delta ET_{Toe\text{-}Finger}$ ($R^2=0.35$, P=0.06) and higher for $PWV_{\Delta PAT\ Toe\text{-}Finger}$ vs $\Delta ET_{Toe\text{-}Finger}$ ($R^2=0.42$, P=0.03). Similar to $\Delta\Delta ET_{Toe\text{-}Finger}$, BMI, HR, and $\Delta PWV_{\Delta PAT\ Toe\text{-}Finger}$ were not correlated with $\Delta ET_{Toe\text{-}Finger}$ (BMI vs $\Delta ET_{Toe\text{-}Finger}$: $R^2=0.03$, P=0.62; HR vs $\Delta ET_{Toe\text{-}Finger}$: $R^2=0.14$, P=0.25; $\Delta PWV_{\Delta PAT\ Toe\text{-}Finger}$ vs $\Delta ET_{Toe\text{-}Finger}$: $R^2=0.00$, P=0.94). The effect of age, BMI, HR, MAP, and $PWV_{\Delta PAT\ Toe\text{-}Finger}$ on $\Delta PWV_{\Delta PAT\ Toe\text{-}Finger}$ may also be explored. All variables were not correlated with $\Delta PWV_{\Delta PAT\ Toe\text{-}Finger}$.

Figure 12A:
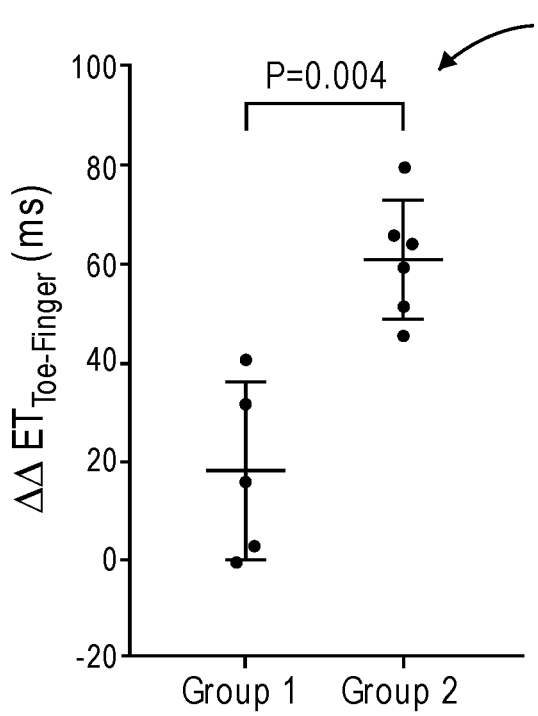
FIGS. 12A-12G illustrate graphs showing subjects that have been divided into two groups according to their percentile rank of the $\Delta\Delta ET_{Toe-Finger}$: group 1 (below 50% of $\Delta\Delta ET_{Toe-Finger}$, mean±SD of 17.9±17.9 ms) and group 2 (above 50% of $\Delta\Delta ET_{Toe-Finger}$, mean±SD of 61.0±12.0 ms) (FIG. 12A). Subjects in group 2 with a higher $\Delta\Delta ET_{Toe-Finger}$ were younger (28±5 years vs 39±8 years, P=0.024) (FIG. 12B), had lower MAPs (74±8 mmHg vs 84±4 mmHg, P=0.022) (FIG. 12E), and tended to have lower $PWV_{\Delta PAT\ Toe-Finger}$ (5.96±1.23 m/s vs 7.16±0.69 m/s, P=0.18) (FIG. 12F) compared to the subjects in group 1 with a lower $\Delta\Delta ET_{Toe-Finger}$. BMI, HR, and $\Delta PWV_{\Delta PAT\ Toe-Finger}$ were not different between the two groups (P=0.43, P=0.33, and P>0.99 respectively) (FIGS. 12C, 12D and 12G).
Figure 12B:
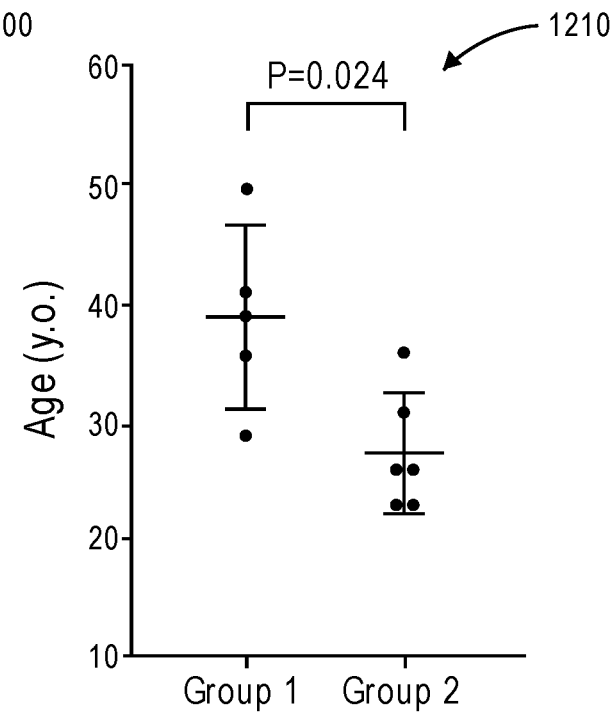
Figure 12C:
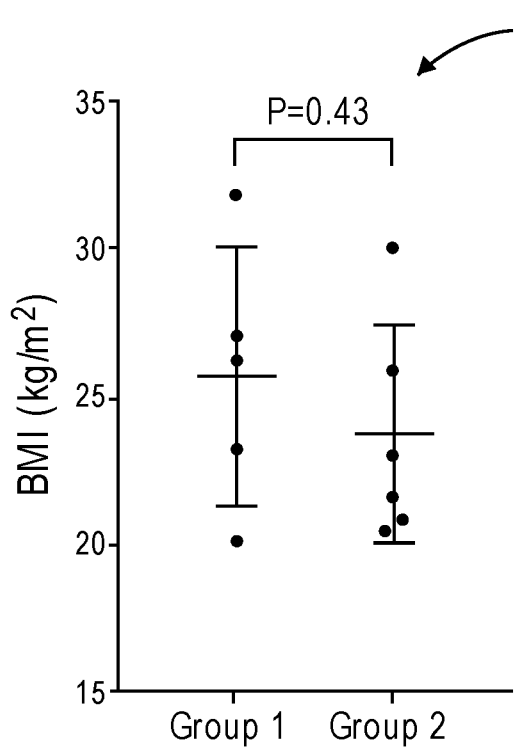
Figure 12D:
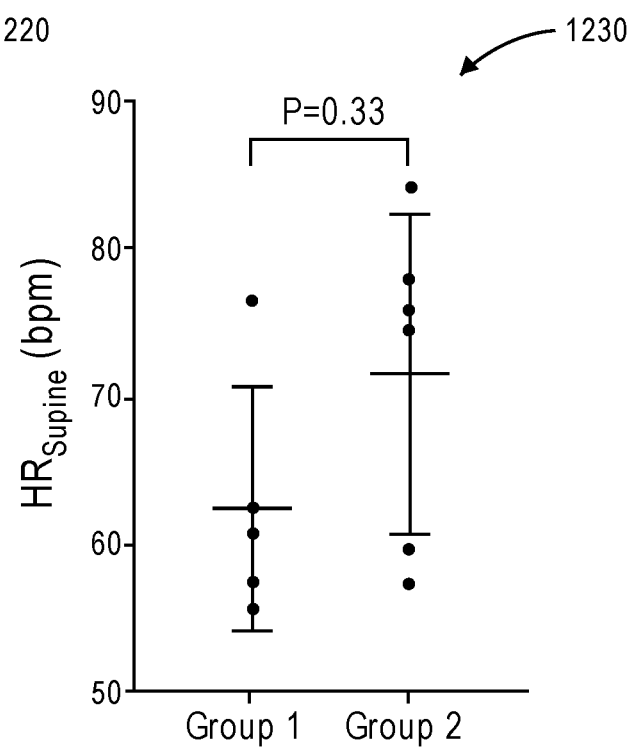
Figure 12E:
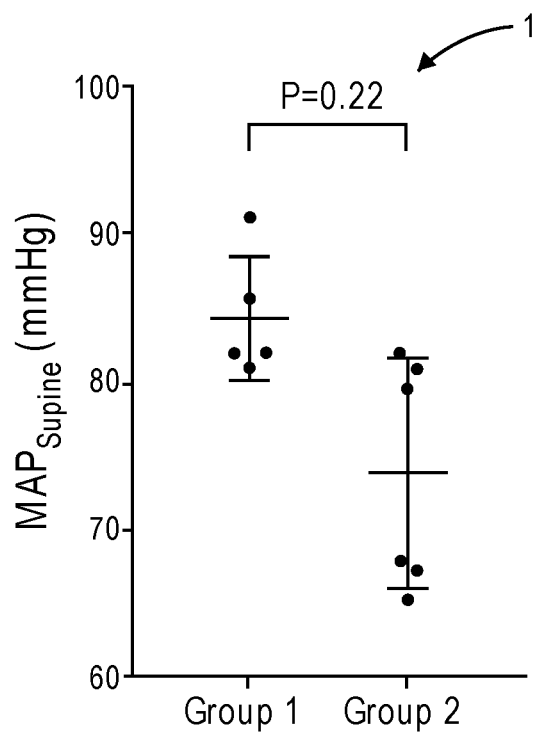
Figure 12F:
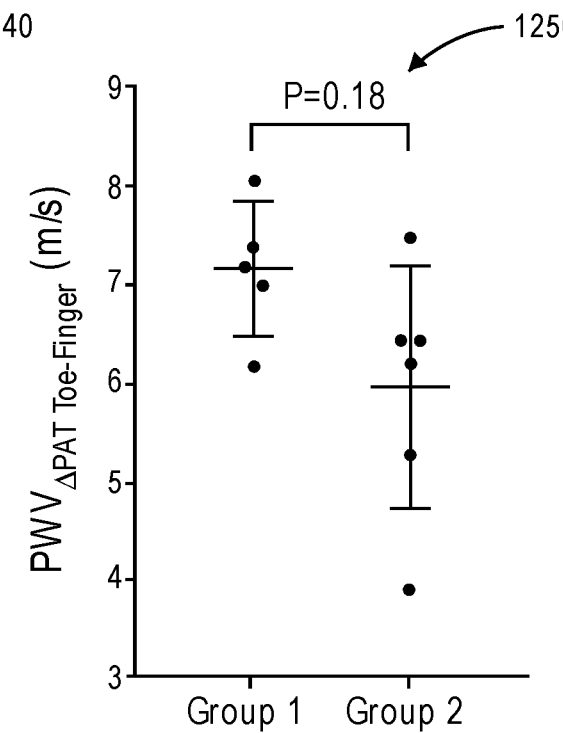
Figure 12G:
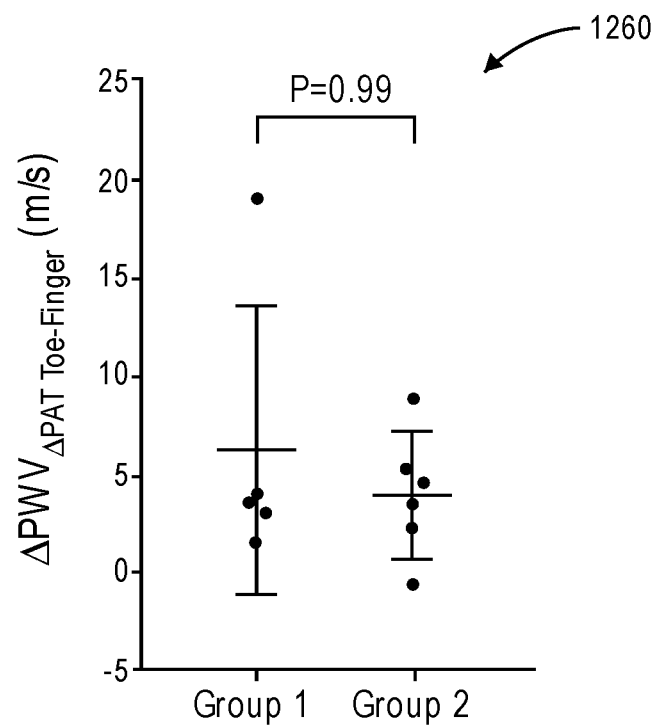

FIGS. 12A-G illustrate graphs 1200, 1210, 1220, 1230, 1240, 1250, 1260 that investigate if $\Delta\Delta ET_{Toe\text{-}Finger}$ could differentiate a more compliant from a less compliant vasculature. The subjects were divided into two groups according to their percentile rank of the $\Delta\Delta ET_{Toe\text{-}Finger}$: group 1 (below 50% of $\Delta\Delta ET_{Toe\text{-}Finger}$, mean±SD of 17.9±17.9 ms) and group 2 (above 50% of $\Delta\Delta ET_{Toe\text{-}Finger}$, mean±SD of 61.0±12.0 ms) (FIG. 12A). Subjects in group 2 with a higher $\Delta\Delta ET_{Toe\text{-}Finger}$ were younger (28±5 years vs 39±8 years, P=0.024) (FIG. 12B), had lower MAPs (74±8 mmHg vs 84±4 mmHg, P=0.022) (FIG. 12E), and tended to have lower $PWV_{\Delta PAT\ Toe\text{-}Finger}$ (5.96±1.23 m/s vs 7.16±0.69 m/s, P=0.18) (FIG. 12F) compared to the subjects in group 1 with a lower $\Delta\Delta ET_{Toe\text{-}Finger}$. BMI, HR, and $\Delta PWV_{\Delta PAT\ Toe\text{-}Finger}$ were not different between the two groups (P=0.43, P=0.33, and P>0.99 respectively) (FIGS. 12C, 12D and 12G).

Figure 13G:
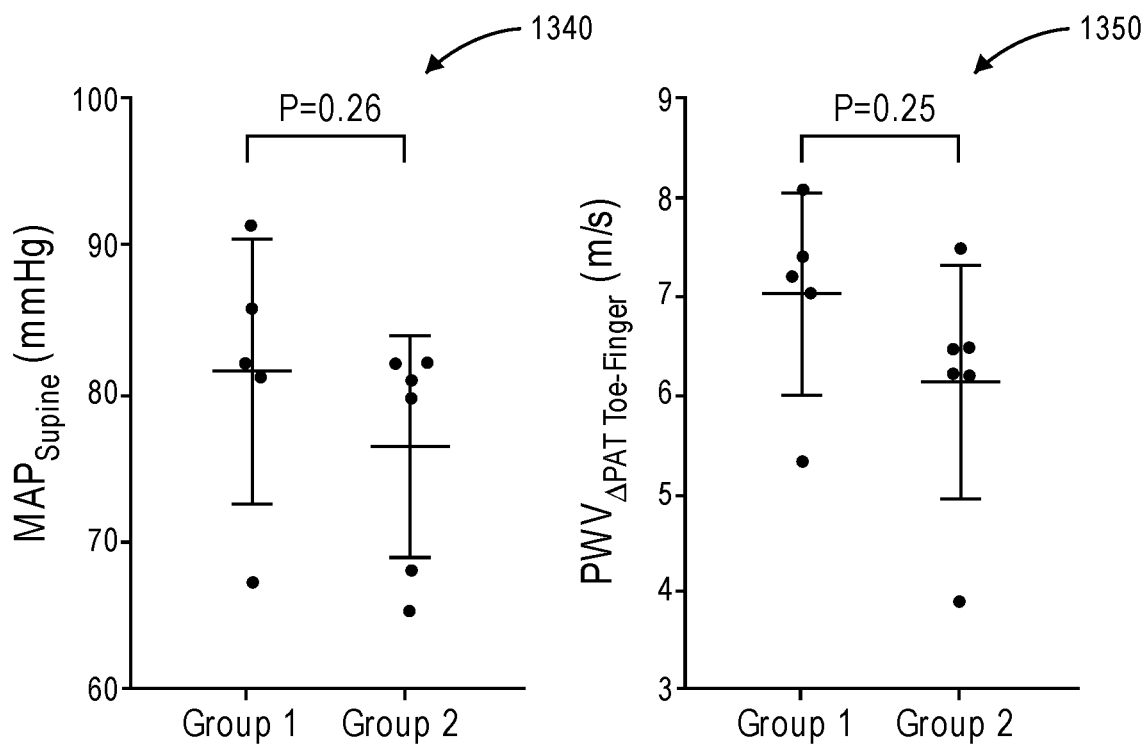
Figure 13G:
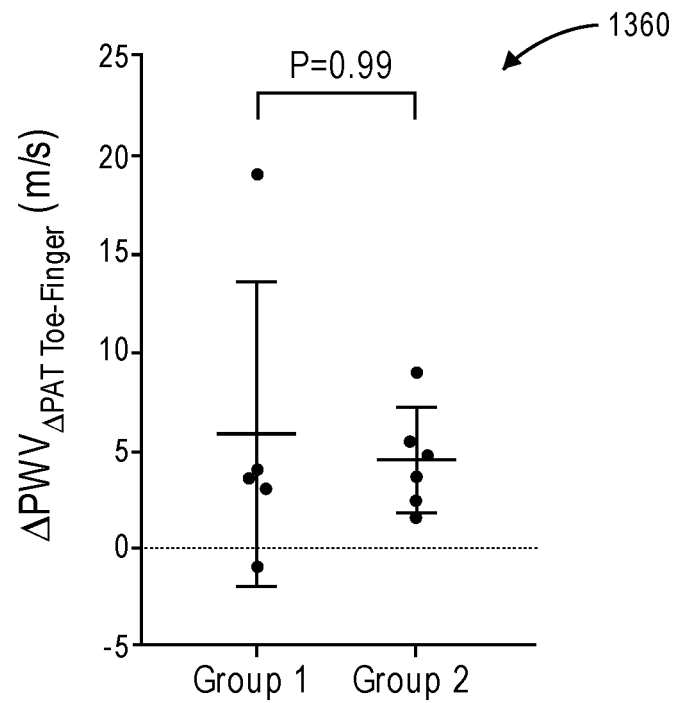

FIGS. 13A-G illustrate graphs 1300, 1310, 1320, 1330, 1340, 1350, 1360 showing different parameters between two groups of subjects with more and less compliant vasculature based on $\Delta\Delta ET_{Toe\text{-}Finger}$. The subjects may be divided into two groups according to their percentile rank of the $\Delta ET_{Toe\text{-}Finger}$ in the supine position to investigate if $\Delta ET_{Toe\text{-}Finger}$ may differentiate a more compliant from a less compliant vasculature similar to $\Delta\Delta ET_{Toe\text{-}Finger}$ (FIG. 13A). Subjects in group 2 with a higher $\Delta ET_{Toe\text{-}Finger}$ tended to be younger (30±10 years vs 36±5 years, P=0.11) (FIG. 13B), have lower MAPs (76±8 mmHg vs 81±9 mmHg, P=0.26) (FIG. 13E), and lower $PWV_{\Delta PAT\ Toe\text{-}Finger}$ (6.12±1.18 m/s vs 6.98±1.03 m/s, P=0.25) (FIG. 13F) compared to subjects in group 1 with a lower $\Delta ET_{Toe\text{-}Finger}$. BMI, HR, and $\Delta PWV_{\Delta PAT\ Toe\text{-}Finger}$ were not different between the group 1 and 2 (P=0.93, P=0.82, and P=0.99 respectively) (FIGS. 13C, 13D and 13G).

Ejection times at the ear, finger, and toe are different for the same heartbeat and become longer as the measurement site distance from the heart increases. Furthermore, the ejection times at individual measurement sites are different in different positions: longest in the supine position and shortest in the standing position. As a result, the difference between ET at different locations (ΔET) for the same heartbeat is maximal for the toe versus the ear in the supine position. This difference becomes smallest in the standing position for all pairs of locations. Moreover, this difference in ETs (ΔET) is distinct in different subjects and correlates with age, blood pressure, PWV, and the corresponding pulse arrival times. Higher values for ΔET in the supine position are generally observed in younger patients with lower MAPs and lower PWVs indicating that the prolongation of the ET at more distal sites (e.g., the toe) compared to more proximal sites (e.g., the ear or finger) might represent an index of vascular properties and ventricular-vascular coupling.

A peripherally measured ET derived from the radial arterial waveform is longer than the centrally measured ET derived from CW Doppler through the aortic valve. Prolongation of the ET at a peripheral site becomes more pronounced at lower BPs and PWVs suggesting a modulating effect of the vasculature on the central ventricular ejection time. The observed difference between ETs at two different peripheral locations appears to be due to the modulating effect of the vasculature on the original central ET and represents intrinsic vascular properties and ventricular-vascular coupling.

Given that the ΔET is longest in the supine position and shortest in the standing position, the difference (ΔΔET) in individual subjects as a potential marker to distinguish a compliant from a stiff vasculature was examined. As by definition, a compliant vasculature is more distensible than a stiff vasculature, and the influence of postural changes on the ET prolongation should be larger in subjects with a compliant vasculature compared to those with a stiff vasculature. There should also be a significant prolongation of the ET measured at the toe in the supine position if the vasculature is compliant. Indeed, both ΔET and ΔΔET are longer in young people with lower blood pressure and lower PWV. Changes in PWV between the supine and standing positions (ΔPWV) do not correlate with either ΔΔET or ΔET. Moreover, in contrast to ΔΔET, ΔPWV does not correlate with age, MAP nor PWV, suggesting that ΔΔET better reflects intrinsic vascular properties. In addition, the $\Delta PWV_{\Delta PAT\ Toe\text{-}Finger}$ difference between the most compliant (8.89 m/s) and stiffest (3.88 m/s) subjects differed by a factor of 2, whereas ΔΔET (79.9 ms in compliant and 15.5 ms in stiff) differed by a factor of 5 for the same subjects indicating that the parameter might potentially be more sensitive to assess arterial stiffness, vascular properties, and ventricular-vascular coupling.

Given that the ΔET in the standing position was small in most subjects and ΔΔET is different between ΔET in the supine vs standing position, it was investigated whether ΔET in the supine position alone will have comparable to ΔΔET correlation with age, MAP and PWV. In fact, ΔET in the supine position had better correlation with $PWV_{\Delta PAT\ Toe\text{-}Finger}$ than ΔΔET, however, worse correlation with age and MAP.

ΔET correlates with the corresponding $PWV_{PAT}$ and $PWV_{DAT}$. Both ΔPAT ($PAT_{Toe\text{-}Finger}$) and $PWV_{\Delta PAT\ Toe\text{-}Finger}$ may be a good alternative for the measurement of arterial stiffness. These findings suggest that both ΔET and ΔΔET are potential markers of vascular properties and support the notion that intra-vascular hydrostatic changes associated with changing position from supine to standing corresponds to significant changes in wall tension and vascular properties. Moreover, ΔET and ΔΔET appear to be more sensitive markers compared to changes in PWV between the supine and standing positions.

Pulse Wave Travel Distance as a Marker of Ventricular-Arterial Coupling

The distance that the front of the pressure waveform travels within the arterial system (i.e., the PWL) may depend both on the PWV and the ET. The PWTD is the product of PWV and ET (PWL=PWV×ET). Applicants tested the hypothesis that ET and peripheral PWV are coupled together, in order to produce a PWTD, which would match the distance from the heart to the most distant site in the arterial system: the toe ($D_{Toe}$). The results from these tests are more fully described in "Pulse Wave Travel Distance as a Novel Marker of Ventricular-Arterial Coupling" by Yurie Obata, Pavel Ruzankin, Allan Gottschalk, Daniel Nyhan, Dan Berkowitz, Jochen Steppan, and Viachaslau Barodka, which is incorporated herein in its entirety.

$ET_{Ear}$ and $PWV_{Toe}$ appear to be coupled in healthy subjects to produce a PWTD that is roughly equivalent to the arterial pathway distance to the toe. Optimal coupling is achieved in the supine position. PWTD may be evaluated further to test its potential as a noninvasive parameter of ventricular-arterial coupling in subjects with cardiovascular diseases. In a healthy vasculature, the product of PWV and ET generate a PWTD that is equal to the length of the maximal arterial distance (i.e., starting at the aortic valve and ending at the most distant site in the arterial tree: the toes).

The VA coupling as a function of PWV and ET was analyzed in relation to the arterial pathway length in healthy volunteers. Postural changes were used to induce changes in PWV and ET to modify PWTD experimentally. Given that PWTD is believed to be matched to the most distant part of the vasculature, the evaluation focused on the most distant portion of the vascular tree (i.e., the toe), using the distance from the heart to the toe as an approximate anatomical vascular distance for comparison. The PWTD was also calculated to more proximal locations, such as the ear and middle finger, for comparison.

Each subject's weight, self-reported height, and the distance from the sternal notch to the ear lobe ($D_{Ear}$), index finger ($D_{Finger}$) and big toe ($D_{Toe}$) was obtained. A standard three-lead EKG was placed in accordance with the American Heart Association (AHA) Scientific Statement. Plethysmography sensors were placed on the left ear lobe, left index finger, and left big toe. The lead II of the EKG and the plethysmograph signals were simultaneously recorded from the ear, finger and toe for 30 seconds each, in the standing, sitting and supine positions. The EKG and plethysmograph signals were digitized at 1 kHz and recorded.

The $ET_{Ear}$ was used as a surrogate for left ventricular ejection time (LVET). Pulse arrival time was obtained by calculating the time delay between the peak of the R wave on the EKG waveform and the initiation of the upstroke on the plethysmograph waveform for toe, finger, and ear: ($PAT_{Toe}$, $PAT_{Finger}$, and $PAT_{Ear}$). PWV was obtained at the toe ($PWV_{Toe}$), PWV was obtained at the finger ($PWV_{Finger}$), and PWV was obtained at the ear ($PWV_{Ear}$). $PWV_{Toe}$ was estimated as the distance from the sternal notch to the big toe ($D_{Toe}$) divided by $PAT_{Toe}$. Furthermore, the pulse wave travel distance ($PWTD_{Toe}$) was calculated as follows: $PWTD_{Toe}=ET_{Ear} \times PWV_{Toe}$ for each position and expressed as a percentage of the $D_{Toe}$ (% $PWTD_{Toe}=PWTD_{Toe}/D_{Toe} \times 100(\%)$).

The findings are depicted in Table 5 below. The difference between $PWTD_{Toe}$ and $D_{Toe}$ in the supine and sitting position were not significantly different from 0 (p=0.96 and p=0.48). Other differences between PWTD and corresponding vascular pathway length (D) were significantly different from 0.

Table 5 shows the mean and 95% CI of PWL, % PWTD, and heart rate (HR) in 3 positions and the differences between the arterial pathway distance (D) and the corresponding Pulse Wave Travel Distance (PWTD). Each p value indicates the significance of differences between PWTD-D and 0. P values printed in boldface type indicate p>0.05.

TABLE 5

| Distance (cm) | PWL (cm) | Standing | | | Sitting | | | Supine | | |
|---|---|---|---|---|---|---|---|---|---|---|
| | | Mean | 95% CI | p | Mean | 95% CI | p | Mean | 95% CI | p |
| $D_{Toe}$ 152.8 | $PWL_{Toe}$ | 136.8 | 129.7, 143.8 | <0.001 | 155.8 | 148.8, 162.9 | 0.48 | 152.6 | 145.7, 159.6 | 0.96 |
| $D_{Finger}$ 88.8 | $PWL_{Finger}$ | 103.5 | 97.5, 109.5 | <0.001 | 118.6 | 112.6, 124.6 | <0.001 | 132.3 | 126.3, 138.2 | <0.001 |
| $D_{Ear}$ 26.6 | $PWL_{Ear}$ | 46.3 | 43.3, 49.4 | <0.001 | 57.2 | 54.1, 60.3 | <0.001 | 70.0 | 66.9, 73.0 | <0.001 |

TABLE 5-continued

| | Standing | | Sitting | | Supine | |
|---|---|---|---|---|---|---|
| | Mean | 95% CI | Mean | 95% CI | Mean | 95% CI |
| % $PWL_{Toe}$ (%) | 89.5 | 84.9, 94.1 | 102 | 97.4, 106.6 | 99.9 | 95.4, 104.5 |
| % $PWL_{Finger}$ (%) | 116.6 | 109.8, 123.3 | 133.6 | 140.3, 149.0 | 149 | 142.2, 155.6 |
| % $PWL_{Ear}$ (%) | 174.1 | 162.8, 185.7 | 215 | 226.7, 263.2 | 263.2 | 251.5, 274.4 |
| HR (bpm) | 84.1 | 77.0, 91.1 | 71.1 | 64.1, 78.1 | 68.2 | 61.2, 75.2 |

The range of the 90% CI to assess the equivalence between the arterial pathway length and PWTD for each location and position are presented in Table 6 below. Equivalence was observed only between $D_{Toe}$ and $PWTD_{Toe}$ in the supine position. 90% CI of the difference between the two ranged from −7.13 cm to +5.10 cm. This range lay within 5% of the average of $D_{Toe}$(±7.64 cm) which is defined as the zone of indifference.

Table 6 assesses equivalencies between the arterial pathway distance and PWTD. 90% CI from equivalence testing indicates the difference between arterial pathway distance (D) and PWTD. Equivalencies are printed in boldface type.

TABLE 6

| | 90% CI from equivalence testing (cm) | | | ±5% of the arterial |
|---|---|---|---|---|
| | Standing | Sitting | Supine | pathway length (cm) |
| $D_{Toe}$ vs $PWL_{Toe}$ | −25.61 to −8.58 | −4.39 to 17.17 | −7.13 to 5.10 | ±7.64 |
| $D_{Finger}$ vs $PWL_{Finger}$ | 7.35 to 21.52 | 24.24 to 37.42 | 35.76 to 49.87 | ±4.42 |
| $D_{Ear}$ vs $PWL_{Ear}$ | 16.66 to 23.19 | 27.69 to 34.29 | 39.14 to 46.44 | ±1.33 |

PWL: pulse wave length; CI: confidence interval.

Figure 14A:
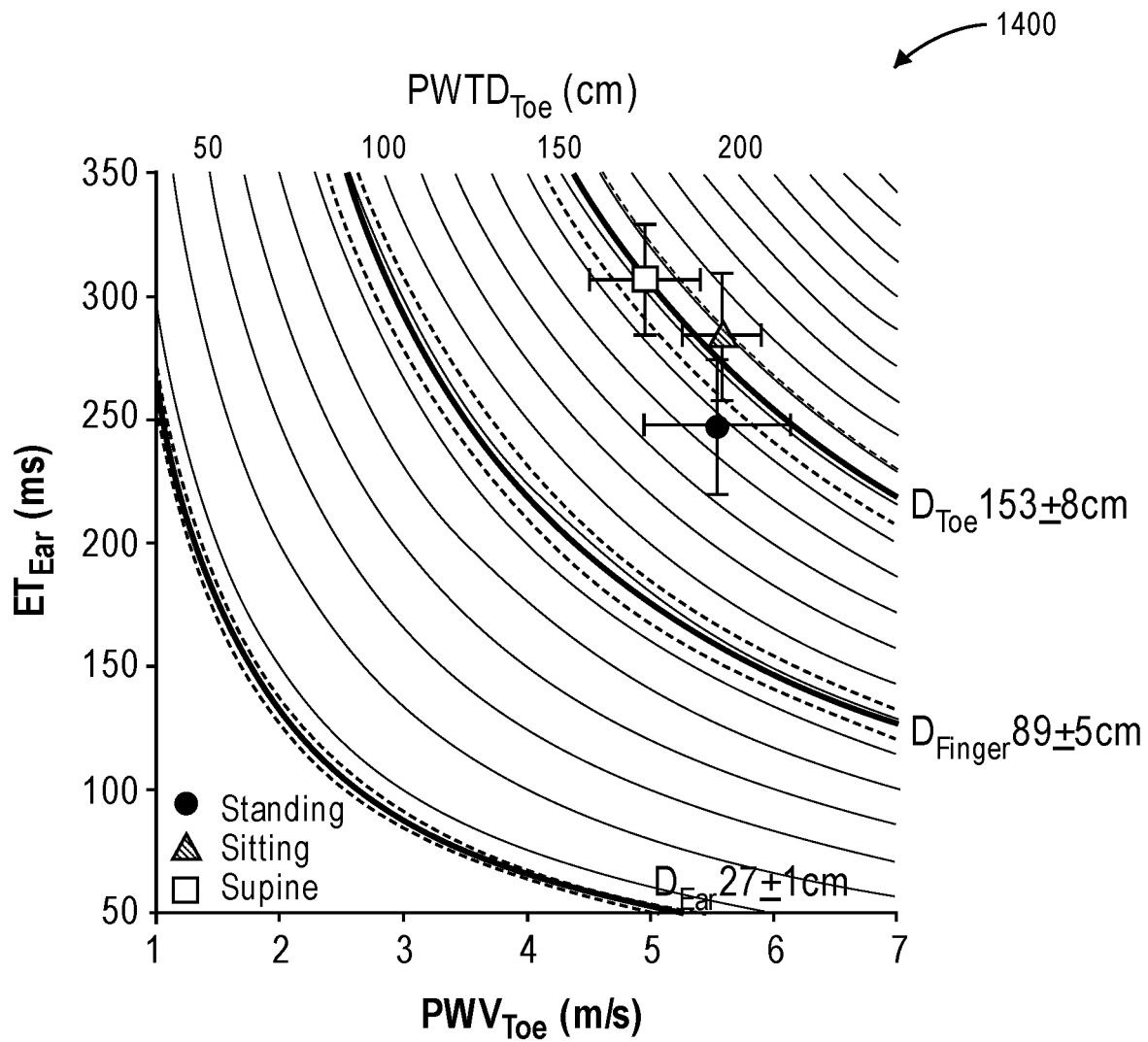
FIGS. 14A-14C depict graphs showing the Pulse Wave Transit Distance (PWTD) to the toe (FIG. 14A), the PWTD to the finger (FIG. 14B), and the PWTD to the ear (FIG. 14C).
Figure 14B:
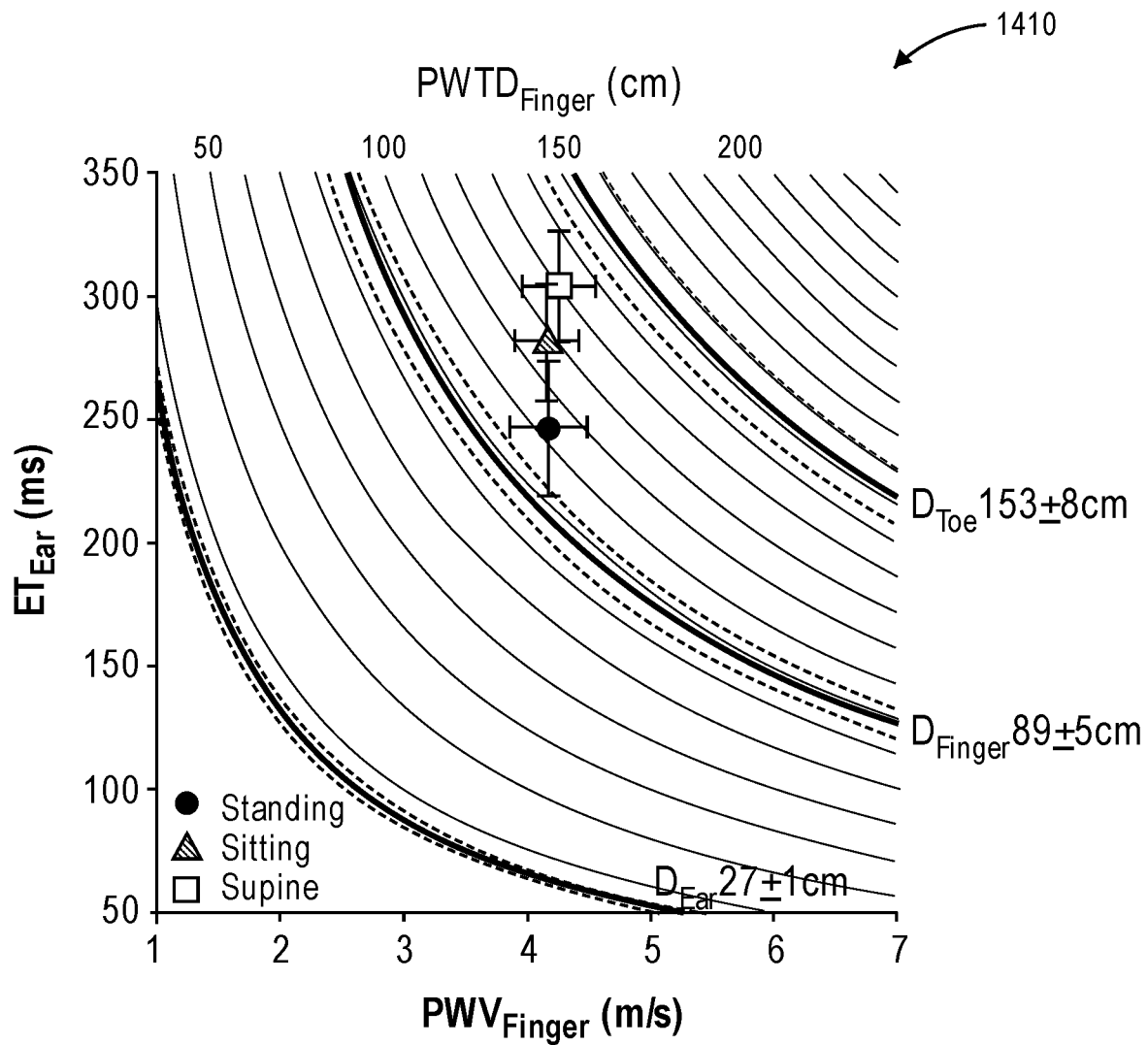
Figure 14C:
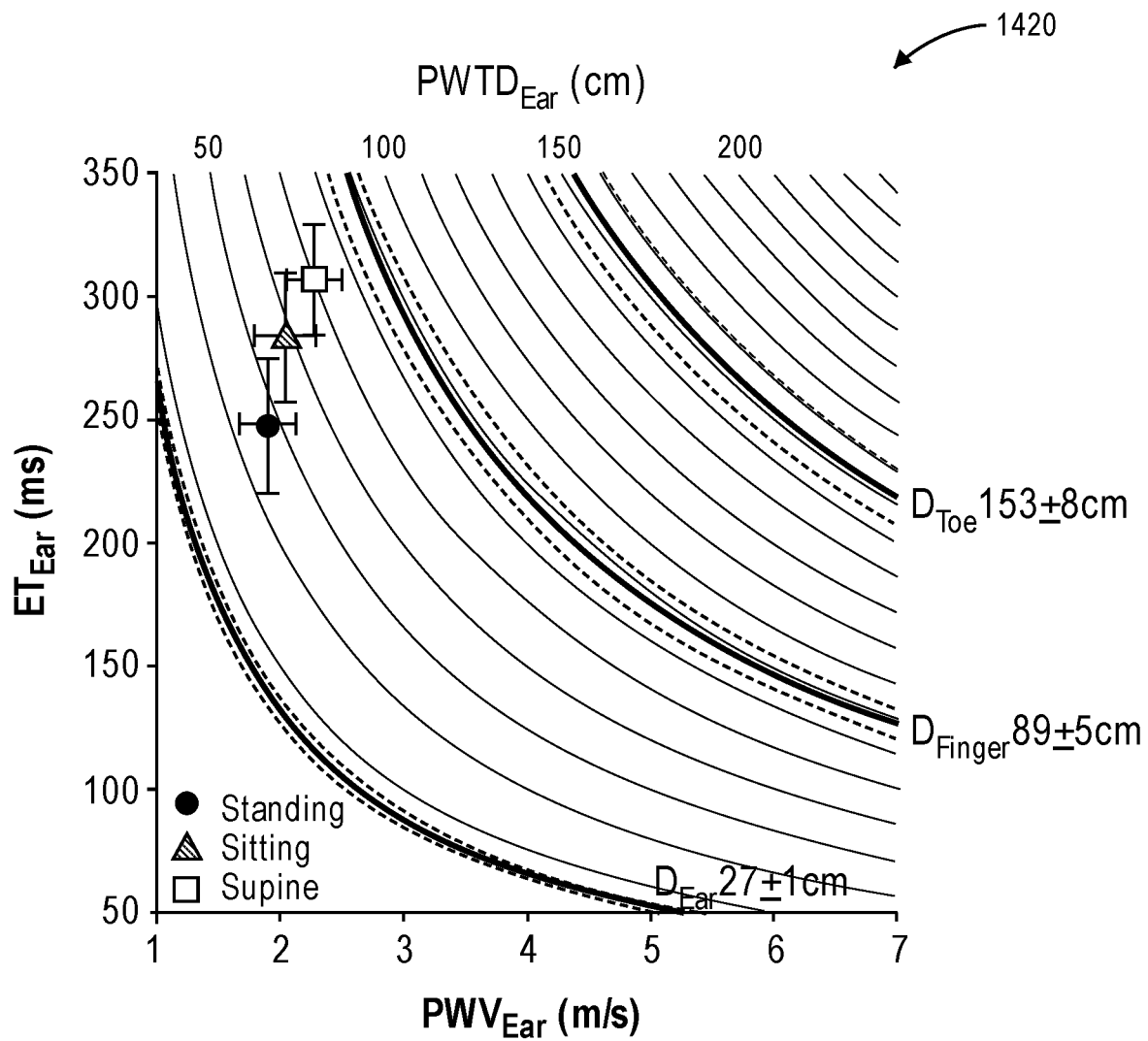

FIGS. 14A-14C depict graphs 1400, 1410, 1420 showing the effects of postural changes on $ET_{Ear}$, PWV, and PWTD. More particularly, the mean with SD error bars of $PWV_{Toe}$ (FIG. 14A), $PWV_{Finger}$ (FIG. 14B), and $PWV_{Ear}$ (Figure C) and corresponding $ET_{Ear}$ derived from all subjects in standing (circle), sitting (triangle) and supine (square) positions is shown. The contour lines on the graphs 1400, 1410, 1420 indicate the $PWTD_{Toe}$ (Figure A), $PWTD_{Finger}$ (Figure B), and $PWTD_{Ear}$ (Figure C) for varying PWV and the corresponding $ET_{Ear}$. The thick solid line and dashed lines indicate mean (SD) of the distance from the sternal notch to the toe $D_{Toe}$ (153±8 cm), finger $D_{Finger}$ (88±4 cm), and ear $D_{Ear}$ (27±1 cm). The calculated $PWTD_{Toe}$ in the supine position is identical to the mean distance from the heart to the toe ($D_{Toe}$). $PWV_{Toe}$ was faster (p=0.002), and $ET_{Ear}$ shorter (p=0.032) when sitting compared to the supine position.

This study supports the hypothesis that, in healthy vasculatures, PWV and ET are coupled to produce a $PWTD_{Toe}$, which closely approximates the anatomical vascular path length from the heart to the toe. When perfect matching exists, and PWTD is equivalent to the anatomical vascular path distance (D), ejection time and pulse arrival time to the peripheral site should be identical, as PWTD was calculated as PWTD=ET×(D/PAT). Indeed, the $ET_{Ear}/PAT_{Toe}$ ratio is 1, and the difference between $ET_{Ear}$ and $PAT_{Toe}$ is 0, indicating the existence of VA coupling in our healthy subjects at the level of the most distant site in the vasculature. An $ET_{Ear}/PAT_{Toe}$ ratio above 1 or $ET_{Ear}/PAT_{Toe}$ difference above 0 indicates overdistension/overfilling of the arterial tree. An $ET_{Ear}/PAT_{Toe}$ ratio below 1 or $ET_{Ear}/PAT_{Toe}$ difference below 0 indicates underfilling/underdistension. The $ET_{Ear}/PAT_{Toe}$ ratio and the difference between $ET_{Ear}$ and $PAT_{Toe}$ reflect matching of the PWTD to the arterial tree length but does not require knowledge of the arterial pathway length itself and might potentially represent an index of left ventricular performance, vascular properties, and/or ventricular-arterial coupling.

One feature of Applicant's approach to describe VA coupling is that pressure overload occurs only after the pulse wave travels the whole arterial tree, and the heart continues to eject. This means that pressure overload occurs towards the end of systole. Also, the contracting heart is the main source of the extra pressure generated. Hence, in addition to the reflected waveforms coming from the periphery, forward pressure waveforms generated by the heart contracting against the fully filled and maximally distended arterial tree may occur. If such secondary forward pressure waveforms in fact exist, they should occur at the end of the systole and before the dicrotic notch and be most prominent in the closest to the heart locations. The amount of pressure overload may be proportional to the mismatch between the actual patient vascular pathway length and the $PWTD_{Toe}$, which will be evidenced by ET being longer than $PAT_{Toe}$ and the $ET_{Ear}/PAT_{Toe}$ ratio above 1. If $PWTD_{Toe}$ is shorter than the real anatomical length of the vasculature, then the pressure and stroke volume generated by the heart would not be able to reach the most distal sites in the vasculature with resultant hypotension in the most distal sites of the arterial tree. If $PWTD_{Toe}$ is longer than $D_{Toe}$, or if ET is longer than $PAT_{Toe}$, then higher pressures are generated and a higher augmentation pressure may be observed. This normal coupling may be disrupted in elderly subjects with increased arterial stiffness, such that $PWTD_{Toe}$ is longer than $D_{Toe}$, the $ET_{Ear}/PAT_{Toe}$ ratio is more than 1, and the $ET_{Ear}-PAT_{Toe}$ difference is positive.

These steps can be carried out using a non-transitory computer readable medium loaded onto a computing device such as a personal computer, tablet, phablet, smartphone, computer server, or any other computing device known to or conceivable by one of skill in the art. Indeed, any suitable hardware and software known to or conceivable by one of skill in the art could be used. The non-transitory computer readable medium can also be incorporated into the device for assessment of PAT.

A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape. The computing device can be a special computer designed specifically for this purpose. The computing device can be unique to the present invention and designed specifically to carry out the method of the present invention.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A device for measuring a ventricular-arterial coupling of a subject, comprising:
    a first input for receiving signals from a plurality of electrocardiogram sensors that are coupled to the subject at a plurality of first locations;
    a second input for receiving signals from a plurality of photoplethysmogram sensors that are coupled to the subject at a plurality of second locations, wherein the second locations are selected from the group consisting of a head of the subject, an arm of the subject, and a leg of the subject, and wherein the signals received from the electrocardiogram sensors and the signals received from the photoplethysmogram sensors are received simultaneously; and
    a monitor configured to display the signals from the electrocardiogram sensors and the signals from the photoplethysmogram sensors, wherein the device is configured to measure:
        a time to arrival between a time at which an aortic valve of the subject opens to a pulse wave arrival at one or more of the second locations; and
        an ejection time, a delta ejection time, and an ejection time index of the subject, wherein the device is configured to determine that the ejection time is different in different parts of a vascular tree of the subject based at least partially upon the delta ejection time and the ejection time index.

2. The device of claim 1, wherein the device is also configured to measure a velocity of the pulse wave and to determine a distance that the pulse wave travels based at least partially upon the ejection time and the velocity of the pulse wave.

3. The device of claim 1, wherein the plurality of first locations are selected from the group consisting of a chest, a shoulder, a torso, and a back of the subject.

4. The device of claim 3, wherein the plurality of second locations comprise a head of the subject, an arm of the subject, and a leg of the subject.

5. The device of claim 3, wherein the plurality of second locations comprise an ear of the subject, a finger of the subject, and a toe of the subject.

6. The device of claim 1, wherein the ejection time comprises a difference between the time to arrival and a dicrotic notch, wherein the dicrotic notch is part of a waveform generated using the signals from the plurality of photoplethysmogram sensors.

7. The device of claim 1, wherein the ejection time is measured via an ultrasound.

8. The device of claim 1, wherein the device is configured to determine a metric related to a distance that the pulse wave travels in an arterial tree of the subject based at least partially upon the time to arrival of the pulse wave at one or more of the second locations.

9. The device of claim 1, wherein the device outputs a single number to quantify how well a distance the pulse wave travels in an arterial tree of the subject during ejection matches an anatomical arterial vasculature path length of the subject.

10. The device of claim 1, further comprising:
    a third input for receiving a signal from an electronic stethoscope sensor that is coupled to the subject; and
    a fourth input for receiving a signal from a blood pressure sensor that is coupled to the subject.

11. A method for measuring a ventricular-arterial coupling of a subject, comprising:
    receiving signals from a plurality of electrocardiogram sensors that are coupled to the subject at a plurality of first locations;
    receiving signals from a plurality of photoplethysmogram sensors that are coupled to the subject at a plurality of second locations, wherein the second locations are selected from the group consisting of a head of the subject, an arm of the subject, and a leg of the subject, and wherein the signals received from the electrocardiogram sensors and the signals received from the photoplethysmogram sensors are received simultaneously;
    determining a time to arrival between a time at which an aortic valve of the subject opens to a pulse wave arrival at one or more of the second locations; and
    determining an ejection time, a delta ejection time, and an ejection time index of the subject, wherein the device is configured to determine that the ejection time is different in different parts of a vascular tree of the subject based at least partially upon the delta ejection time and the ejection time index.

12. The method of claim 11, wherein the signals from the plurality of photoplethysmogram sensors are received when the subject is in a standing position, a sitting position, and a supine position.

13. The method of claim 11, wherein the plurality of second locations comprise a head of the subject, an arm of the subject, and a leg of the subject.

14. The method of claim 11, wherein the plurality of second locations comprise an ear of the subject, a finger of the subject, and a toe of the subject.

15. The method of claim 14, further comprising determining a velocity of the pulse wave between the finger and the toe.

16. The method of claim 11, further comprising determining a metric related to reception and distribution of a volume of the pulse wave by an arterial tree of the subject based at least partially upon the time to arrival of the pulse wave from the heartbeat of the subject to the one or more second locations.

17. The method of claim 16, further comprising outputting a single number to quantify how well a distance the pulse wave travels in the arterial tree of the subject during ejection matches an anatomical arterial vasculature path length.

18. The method of claim 11, further comprising determining a difference between a travel distance of the pulse wave and an anatomical distance from a heart of the subject to a most distal site in the arterial tree when the subject is in different positions based on the signals from the plurality of electrocardiogram sensors and the signals from the plurality of photoplethysmogram sensors.

19. The method of claim 11, further comprising determining a difference in time between the ejection time and a pulse arrival time to a toe.

20. The method of claim 11, further comprising:
   determining a velocity of the pulse wave, wherein the velocity and the ejection time are determined simultaneously; and
   determining a travel distance of the pulse wave based at least partially upon the velocity and the ejection time.

\* \* \* \* \*